US006093549A

United States Patent [19]

Ross et al.

[11] Patent Number: 6,093,549

[45] Date of Patent: Jul. 25, 2000

[54] HUNTINGTIN-ASSOCIATED PROTEIN-RELATED ASSAYS

[75] Inventors: Christopher A. Ross; Xiao-Jiang Li; Shi-Hua Li; Alan H. Sharp; Anthony Lanahan; Paul F. Worley; Solomon H. Snyder, all of Baltimore, Md.

[73] Assignee: The Johns Hopkins University, Baltimore, Md.

[21] Appl. No.: 08/556,419

[22] Filed: Nov. 9, 1995

[51] Int. Cl.[7] .................................................. G01N 33/53

[52] U.S. Cl. .................................................. 435/7.1

[58] Field of Search .................................................. 435/7.1

[56] References Cited

U.S. PATENT DOCUMENTS 5,366,889 11/1994 MacDonald et al. ................ 435/252.3

FOREIGN PATENT DOCUMENTS

| | | |
|---|---|---|
| 0 614 977 A2 | 3/1994 | European Pat. Off. . |
| 0 617 125 A2 | 3/1994 | European Pat. Off. . |
| 94/21790 | 3/1994 | WIPO . |
| 94/24279 | 4/1994 | WIPO . |

OTHER PUBLICATIONS

Li et al., Nature, vol. 378, Nov. 23, 1995, pp. 398–402; "A huntingtin–associated protein enriched in brain with implications for pathology".

Ross C. et al., The American Journal of Human Genetics, vol. 57, No. 4, Oct. 1995, p. 41, "Huntington's disease (HD): Involvement of the HD protein and identification of a cDNA coding for an associated protein (HAP–1)".

The Huntington's Disease Collaborative Research Group Cell, vol. 72, No. 6, Mar. 26, 1993, pp. 971–983, "A novel gene containing a trinucleotide repeat that is expanded and unstable on Huntington's disease chromosomes".

Chien et al., "The Two–Hybrid System: A Method to Identify and Clone Genes for Proteins that Interact with a Protein of Interest", *Proc. Natl. Acad. Sci. USA,* 88:9578–9582 (1991).

Chevray et al., "Protein Interaction Cloning in Yeast: Identification of Mammalian Proteins that React with the Leucine Zipper of Jun", *Proc. Natl. Acad. Sci. USA,* 89:5789–5793 (1992).

Fearon et al., "Karyoplasmic Interaction Selection Strategy: A General Strategy to Detect Protein–Protein Interactions in Mammalian Cells", *Proc. Natl. Acad. Sci. USA,* 89:7958–7962 (1992).

Fields et al., "The Two–Hybrid System: An Assay for Protein–Protein Interactions", *TIG 10*(8):286–292 (1994).

Ross, "When More Is Less: Pathogenesis of Glutamine Repeat Neurodegenerative Diseases", *Neuron 15*:493–496 (1995).

Rudinger, In "Peptide Hormones." Jun. 1976, ed. J.A. Parsons, University Park Press, Baltimore, pp. 1–7.

*Primary Examiner*—Anthony C. Caputa
*Assistant Examiner*—Robert C. Hayes
*Attorney, Agent, or Firm*—Banner & Witcoff, Ltd.

[57] ABSTRACT

Proteins which specifically bind to huntingtin, the product of the Huntington's Disease locus (HD), are used in assays for screening drug candidates. These proteins, termed huntingtin associated proteins, bind to huntingtins of both normal and Huntington's Disease patients. However, the binding is stronger to the huntingtins from the patients. The strength of binding correlates with the number of glutamine repeats in the huntingtin, which itself correlates with the time of disease onset.

40 Claims, 15 Drawing Sheets

Fusion proteins Input Binding Input +GST-HAP1

FIG. 2b

| | | |
|---|---|---|
| MRPKDQVQSSAGDGTGSGDPATGTPTTQPAADPAPEPSAEPKPAPAQGTG | 50 | |
| SGQKSGSRTKTGGSFCRSRIRGDSDAPWTRYIFQGPYGPRATGLGTGRAE | 100 | |
| GIWKTPAAYIGRRPGVSGPERAAFIRELQEALCPNPLPRKKITEDDIKVM | 150 | |
| LYLLEEKERDLNTAARIGQSLVKQNSVLMEENNKLETMLGSAREEILHLR | 200 | |
| KQVNLRDDLLQLYSDSDDDEEDEEDEEEEEGEEEEREGQRDQDQQHDHPY | 250 | |
| GAPKPPPKAETLHHCPQLEALKQKLK**LLEEENDHLREEASHLDNLEDKEQ** | 300 | |
| **MLILECVEQFSEASQQMAELSEVLVLRLEGYERQQKEITQLQAEITKLQQ** | 350 | |
| **RCQSYGAQTEKLQQQLASEKGVHPESLRAGSHMQDYGSRPRERQEDGKSH** | 400 | |
| **RQRSSMPAGSVTHYGYSVPLDALPSFPETLAEELRTSLRKFITDP**AYFME | 450 | |
| RCDTRCREERKKEQGTMPPPPVQDLKPPEDFEAPEELVPEEELGAIEEVG | 500 | |
| TAEDGPAEETEQASEETEAWEEVEPEVDEATRMNVVVSALEASGLGPSHL | 550 | |
| DMKYVLQQLSNWQDAHSKRQQKQKVVPKGECSRRGHPPASGTSYRSSTL* | 599 | **rHAP1-A** |
| DSPAPQQQTNMGGGIVEQQPIV | 600 | |
| PTQDSQRLEEDRATHSPSAREEEGPSGAT* | 629 | **rHAP1-B** |

FIG. 2c

```
hHLP1    (1)    DDLLQLYSDSDEEDEDEEEEEEEFKEAEEEQEEEEAEEDLQCAHPCDAPKLISQEALLHQHHCP
rHAP1-A (157)   DDLLQLYSDSDDDEEDEEDEEEE-EGEEEEREGQRDQDQQHDHPYGAPKPPPKAETL--HHCP

hHLP1           QLEALQEKLRLLEEENHQLREEASQLDTLEDEEQMLILECVEQFSEASQQMAELSEVLVL
rHAP1-A         QLEALKQKLKLLEEENDHLREEASHLDNLEDKEQMLILECVEQFSEASQQMAELSEVLVL
hHAP1       (1) KLKLLEEENHQLREEASQLDTLEDEEQMLILECVEQFSEASQQMAELSEVLVL

hHLP1           RLENYERQQQEVARLQAQVLKLQQRCRMYGAETEKLQKQLASEKEIQMQ-L---------
rHAP1-A         RLEGYERQQKEITQLQAEITKLQQRCQSYGAQTEKLQQQLASEKGVHPESLRAGSHMQDY
hHAP1           RLEGYERQQKEITQLQAEITKLQQRCQSYGAQTEKLQQQLASEKGVHPESLRAGSHMQDY

hHLP1           ----------------------------------ETLPGFQETLAEELRTSLRRMISDPV
rHAP1-A         GSRPRERQEDGKSHRQRSSMPAGSVTHYGYSVPLDALPSFPETLAEELRTSLRKFITDPA
hHAP1           GSRPRERQEDGKSHRQRSSMPAG(136)

hHLP1           YFMERNYEMPRGDTSSLRYDFRYSEDREQVRGFEAEEGLMLAADIMRGEDFTPAEELVPQEEL
rHAP1-A         YFMER-------------CDTRCREERKKEQG---TMPPPPVQDLKPPEDFEAPEELVPEEEL

hHLP1           GAAKKV-PAEEGVMEEAELVSEETEGWEEVELELDEATRMNVVTSTLEASGLGPSHLDMNYVLQQLS(328)
rHAP1-A         GAIEEVGTAEDGPAEETEQASEETEAWEEVEPEVDEATRMNVVVSALEASGLGPSHLDMKYVLQQLS(560)
```

FIG. 5a-1 rHAP1-A U38370 translation="MRPKDQVQSSAGDGTGSGDPATGTPTTQPAADPAPEPSAEPKPA
PAQGTGSGQKSGSRTKTGGSFCRSRIRGDSDAPWTRYIFQGPYGPRATGLGTGRAEGI
WKTPAAYIGRRPGVSGPERAAFIRELQEALCPNPLPRKKITEDDIKVMLYLLEEKERD
LNTAARIGQSLVKQNSVLMEENNKLETMLGSAREEILHLRKQVNLRDDLLQLYSDSDD
DEEDEEDEEEEEGEEEEREGQRDQDQQHDHPYGAPKPPPKAETLHHCPQLEALKQKLK
LLEEENDHLREEASHLDNLEDKEQMLILECVEQFSEASQQMAELSEVLVLRLEGYERQ
QKEITQLQAEITKLQQRCQSYGAQTEKLQQQLASEKGVHPESLRAGSHMQDYGSRPRE
RQEDGKSHRQRSSMPAGSVTHYGYSVPLDALPSFPETLAEELRTSLRKFITDPAYFME
RCDTRCREERKKEQGTMPPPPVQDLKPPEDFEAPEELVPEEELGAIEEVGTAEDGPAE
ETEQASEETEAWEEVEPEVDEATRMNVVVSALEASGLGPSHLDMKYVLQQLSNWQDAH
SKRQQKQKVVPKGECSRRGHPPASGTSYRSSTL"

FIG. 5a-2

```
   1 ggaattcggc acgaggcgac agcggactgc agagtcaaga tgcgcccgaa ggaccaggtg
  61 cagagcagtg ccggggacgg gacggggtcg ggggacccag caacaggcac ccccacgacc
 121 cagcctgcag cggatcccgc tccggagccc tcggcagagc ccaaacctgc tccggcgcag
 181 ggaaccgggt ccggacagaa atcaggatcc cgaaccaaga caggaggaag cttttgtagg
 241 tccaggatcc gtggcgactc ggacgcacca tggacccgct acatattcca ggggccttac
 301 ggtccccggg ctactggcct gggcactgga agggctgagg gaatctggaa gacgccagcc
 361 gcgtacatcg gccgaaggcc cggcgtgtcc ggccctgagc gcgcggcgtt tattcgagag
 421 ctgcaggaag cgctgtgtcc taatccactg cccaggaaga agatcaccga agatgatatc
 481 aaagtgatgt tgtatttgct ggaagagaaa gaacgggacc tgaacacagc cgctcgcatc
 541 ggccagtccc tggtgaaaca gaatagtgtt ctgatggagg agaataacaa gctggaaacc
 601 atgctgggct cagccagaga ggagatttta catctccgga agcaggtgaa cctgcgagat
 661 gatctccttc agctctactc ggactccgat gacgatgagg aggatgaaga ggatgaggaa
 721 gaggaagagg gagaagagga ggaacgagaa ggacagaggg accaagatca gcagcacgac
 781 catccctatg gtgcccccaa gccgcccct aaggctgaga cgctgcacca ctgcccacag
 841 ctggaagccc tgaagcagaa gctgaaactg ctggaagaag agaacgacca tcttcgagag
 901 gaggcctccc accttgacaa cctggaagac aaagaacaga tgctcattct ggagtgtgtg
 961 gaacagtttt ctgaagccag ccagcagatg gcagagctat ccgaggtgtt ggtgctgagg
1021 ctggaaggct atgagaggca gcagaaggag atcactcagc tgcaggccga gatcaccaag
1081 ctacaacagc gttgtcagtc ttatggggcc cagacggaga aactgcagca gcagctggcc
1141 tcagagaagg gagtccaccc agagagcctg cgagctggct cccacatgca ggattatgga
1201 agcaggcctc gtgaacgcca ggaggatggg aagagccatc gtcagcgttc ctcaatgcct
1261 gcaggttctg tcacccacta tggatacagt gtgcctctgg atgcacttcc aagtttccca
1321 gagacactgg cggaggagct ccggacatcc ctgaggaagt tcatcactga ccctgcgtat
1381 ttcatggaga gatgtgacac tcgctgcaga gaggaacgaa agaaggagca ggggacaatg
1441 ccaccccac cggtgcaaga tctcaagccg cctgaagatt tcgaggctcc agaggagctg
```

FIG. 5a-3

```
1501 gttcctgagg aggagctggg ggccatagaa gaggtgggga cagctgagga tgggccggca
1561 gaagagacag agcaggcatc tgaggagacc gaggcctggg aggaggtgga accggaggtg
1621 gacgaggcca caaggatgaa tgtggtggtc tctgccctgg aggccagcgg cctgggccct
1681 tcacacctgg acatgaagta tgtcctccag caactgtcca actggcagga cgcccattct
1741 aagcggcagc agaagcagaa ggtggtcccg aaaggtgagt gttcccgcag aggacaccct
1801 cctgccagtg ggacaagcta ccgatcatca accctatgag aggtgagagt aggtgagacc
1861 ccccaccccc aagggctcac ttacctcacc ttggtcccac tcggtgtgct gatttgcatg
1921 gactttgcat actatttgca tagtatttac atacttgcct ccagtccccc ttggctagaa
1981 ctgctgcctc agtgtttatt tatgcaaaat ttgcttacaa gtccagctat ccatccacct
2041 tcttcctggg gggctgaac tgggaatcag ggttggacta tacactcctt tgtacctcaa
2101 cttcctgtct ctgcccatcc tctccctatc cccaattcct ctaccctcaa gactccccag
2161 ccccgcagca gcaaacaaac atgggggcg ggatcgtgga gcagcagccc atagtgccga
2221 cccaggactc tcagaggctg gaggaggaca gggccactca ctctcccagt gccagggagg
2281 aagaggggcc ttctggggcc acctaggcct ggaacgaagg cctctgccag caaaggccac
2341 agttggacca atcccccggg tgagtgtggg gctcccgcag ggtggtaggg gcgggtcagg
2401 gtctcctctg cctatctgga aaccccagtt cctaggagat gctgtccgtg aaatcagatg
2461 atttagcatt ggatctcttt ctgtgttagc tcctttcgtc ttctggccct gtgggtgggt
2521 ggatgtgatt gtgcaccatt tattagaaga ggaatctgaa gttcagagat ctgagatgac
2581 ttggccaagg tcatacagct aggagcagat ctgagccggt gtctcttgag gactgaaacc
2641 ctggcctggt ctcactgccg tccacacctc ctcctgctcc cgtccttgag ctccacctga
2701 agctttggca gcctccctca tgtcggtctg ttgccatttt tgggggcac cagtgagtgg
2761 aacatcactg gctgcagcac agtcaaatca tgcaggttgt aagctgagtc agcacacccg
2821 tggctgacca cgggagaccg ggagacctga gtaacggcta gcggtggctt tctgttgtct
2881 cctgacccgg ctgactgggt ttgagggtga tctgtctccc ggttcacccc cttctcttcc
2941 tggctttgct gtttctcagc agcctgaaga agaccctcag acagctcgag acccctcctt
```

FIG. 5b-I

```
3001 ccactgcctg gccaagtccg acccttcctt gctttcctct gagacaggac ccccaccccc
3061 atgtctgtca gcagttctcc ctctgtcttg atagatcttt cccctcttgt aggacaggct
3121 gaaagaaccc cagtccctca ttctgaaact ggggccaaag ctgtgcctgc tggagcccca
3181 gggggtggaa gcaacctgtg ggtagattgg ttggttacca gacccagctc tgagatggtg
3241 tgggtgcgca catccctagg gtaggcagtt attgggggga ccctttctat cccttgaacc
3301 tctcacgtaa agggacttcc ccagtcctgg ttggcttttg gaacctggtc cttcttgctg
3361 tttttaccc ttccccgttt ctattactgc gtgtaacgta aagtgtatct gagtgagggt
3421 ggtgggaacc ctctgtccag tgctgtctct gtctcccatg gcctgtgagt ttccttctag
3481 agttctactc ttctccacct ctttgctcat acagagctgt ggccttggcg cctgccctgc
3541 ttctgcagtg cttcattgtc tcgtagcttg tcagctgaca ccggaaccgc ggacgggacg
3601 aagacgtcac gaagtaacag agcatcgaac agtcgatttg tattgatgta tgtgccaatg
3661 tgggaaataa agaccttgtg agataaaaaa aaaaaaaaaa aaaaaaaa
```

FIG. 5b-2 rHAP1-B U38371

```
   1 ggaattcggc acgaggcgac agcggactgc agagtcaaga tgcgcccgaa ggaccaggtg
  61 cagagcagtg ccggggacgg gacggggtcg ggggacccag caacaggcac ccccacgacc
 121 cagcctgcag cggatcccgc tccggagccc tcggcagagc ccaaacctgc tccggcgcag
 181 ggaaccgggt ccggacagaa atcaggatcc cgaaccaaga caggaggaag cttttgtagg
 241 tccaggatcc gtggcgactc ggacgcacca tggacccgct acatattcca ggggccttac
 301 ggtccccggg ctactggcct gggcactgga agggctgagg gaatctggaa gacgccagcc
 361 gcgtacatcg gccgaaggcc cggcgtgtcc ggccctgagc gcgcggcgtt tattcgagag
 421 ctgcaggaag cgctgtgtcc taatccactg cccaggaaga agatcaccga agatgatatc
 481 aaagtgatgt tgtatttgct ggaagagaaa gaacgggacc tgaacacagc cgctcgcatc
 541 ggccagtccc tggtgaaaca gaatagtgtt ctgatggagg agaataacaa gctggaaacc
 601 atgctgggct cagccagaga ggagatttta catctccgga agcaggtgaa cctgcgagat
 661 gatctccttc agctctactc ggactccgat gacgatgagg aggatgaaga ggatgaggaa
 721 gaggaagagg gagaagagga ggaacgagaa ggacagaggg accaagatca gcagcacgac
 781 catccctatg gtgcccccaa gccgcccccct aaggctgaga cgctgcacca ctgcccacag
 841 ctggaagccc tgaagcagaa gctgaaactg ctggaagaag agaacgacca tcttcgagag
 901 gaggcctccc accttgacaa cctggaagac aaagaacaga tgctcattct ggagtgtgtg
 961 gaacagtttt ctgaagccag ccagcagatg gcagagctat ccgaggtgtt ggtgctgagg
1021 ctggaaggct atgagaggca gcagaaggag atcactcagc tgcaggccga gatcaccaag
1081 ctacaacagc gttgtcagtc ttatggggcc cagacggaga aactgcagca gcagctggcc
1141 tcagagaagg gagtccaccc agagagcctg cgagctggct cccacatgca ggattatgga
1201 agcaggcctc gtgaacgcca ggaggatggg aagagccatc gtcagcgttc ctcaatgcct
1261 gcaggttctg tcacccacta tggatacagt gtgcctctgg atgcacttcc aagtttccca
```

FIG. 5b-3

```
1321 gagacactgg cggaggagct ccggacatcc ctgaggaagt tcatcactga ccctgcgtat
1381 ttcatggaga gatgtgacac tcgctgcaga gaggaacgaa agaaggagca ggggacaatg
1441 ccacccccac cggtgcaaga tctcaagccg cctgaagatt tcgaggctcc agaggagctg
1501 gttcctgagg aggagctggg ggccatagaa gaggtgggga cagctgagga tgggccggca
1561 gaagagacag agcaggcatc tgaggagacc gaggcctggg aggaggtgga accggaggtg
1621 gacgaggcca caaggatgaa tgtggtggtc tctgccctgg aggccagcgg cctgggccct
1681 tcacacctgg acatgaagta tgtcctccag caactgtcca actggcagga cgcccattct
1741 aagcggcagc agaagcagaa ggtggtcccg aaagactccc cagccccgca gcagcaaaca
1801 aacatggggg gcgggatcgt ggagcagcag cccatagtgc cgacccagga ctctcagagg
1861 ctggaggagg acagggccac tcactctccc agtgccaggg aggaagaggg gccttctggg
1921 gccacctagg cctggaacga aggcctctgc cagcaaaggc cacagttgga ccaatccccc
1981 ggctcctttc gtcttctggc cctgtgggtg ggtggatgtg attgtgcacc atttattaga
2041 agaggaatct gaagttcaga gatctgagat gacttggcca aggtcataca gctaggagca
2101 gatctgagcc ggtgtctctt gaggactgaa accctggcct ggtctcactg ccgtccacac
2161 ctcctcctgc tcccgtcctt gagctccacc tgaagctttg gcagcctccc tcatgtcggt
2221 ctgttgccat tttggggggg caccagtgag tggaacatca ctggctgcag cacagtcaaa
2281 tcatgcaggt tgtaagctga gtcagcacac ccgtggctga ccacgggaga ccgggagacc
2341 tgagtaacgg ctagcggtgg ctttctgttg tctcctgacc cggctgactg ggtttgaggg
2401 tgatctgtct cccggttcac ccccttctct tcctggcttt gctgtttctc agcagcctga
2461 agaagaccct cagacagctc gagacccctc cttccactgc ctggccaagt ccgacccttc
2521 cttgctttcc tctgagacag gacccccacc cccatgtctg tcagcagttc tccctctgtc
2581 ttgatagatc tttcccctct tgtaggacag gctgaaagaa ccccagtccc tcattctgaa
2641 actggggcca aagctgtgcc tgctggagcc ccagggggtg gaagcaacct gtgggtagat
2701 tggttggtta ccagacccag ctctgagatg gtgtgggtgc gcacatccct agggtaggca
2761 gttattgggg ggaccctttc tatcccttga acctctcacg taaaggact tccccagtcc
```

FIG. 5c-l

```
2821 tggttggctt ttggaacctg gtccttcttg ctgtttttta cccttccccg tttctattac
2881 tgcgtgtaac gtaaagtgta tctgagtgag ggtggtggga accctctgtc cagtgctgtc
2941 tctgtctcct atggcctgtg agtttccttc tagagttcta ctcttctcca cctctttgct
3001 catacagagc tgtggccttg gcgcctgccc tgcttctgca gtgcttcatt gtctcgtagc
3061 ttgtcagctg acaccggaac cgcggacggg acgaagacgt cacgaagtaa cagagcatcg
3121 aacagtcgat ttgtattgat gtatgtgcca atgtgggaaa taaagacctt gtgagataaa
3181 aaaaaaaaaa aaaaaaaaaa a
```

hHLP1 U38372

```
  1 ctctactcag attctgatga ggaggatgag gatgaagaag aggaggagga agaaaaggag
 61 gcagaagagg aacaggaaga agaagaagca gaggaagacc tgcagtgtgc tcatccctgt
121 gatgccccta agctgatttc gcaggaggca ttgctgcacc agcaccactg cccacagctg
181 gaagccttgc aggagaagct gaggctgctg gaggaggaga atcatcagct gagagaagag
241 gcctctcaac tcgacactct tgaggatgag gaacagatgc tcattctgga gtgtgtggag
301 cagttttcgg aggccagcca acagatggct gagctgtcgg aggtgctggt gctcaggctg
361 gaaaactatg aacggcagca gcaggaggtc gctcggctgc aggcccaggt gctgaagctg
421 cagcagcgct gccggatgta tggggctgag actgaaaagt tgcagaagca gctggcttcg
481 gagaaggaaa tccagatgca gctccaggaa gaggagactc tgcctggttt ccaggagacg
541 ctggctgagg agctcagaac gtctctaagg aggatgatct cagaccctgt gtattttatg
601 gagaggaatt atgagatgcc cagaggggac acatccagcc taaggtatga ttttcgctac
661 agtgaggatc gagagcaggt gcgggggttt gaggctgagg aagggttgat gctggcagcg
721 gatatcatgc gggggggaaga tttcacgcct gcggaggagt tggtgcccca ggaggagctg
781 ggggctgcca agaaggtgcc ggctgaggaa ggggtgatgg aagaggcaga gctggtgtca
841 gaggagaccg agggctggga ggaggtggaa ctggagctgg atgaggcaac gcggatgaac
901 gtggtgacat caaccctgga ggccagcggc ttgggccctt cacacctgga catgaattat
```

FIG. 5c-2 hHAP1 U38373

```
  1 gaggaggaga atcatcagct gagagaagag gcctctcaac tcgacactct tgaggatgag
 61 gaacagatgc tcattctgga gtgtgtggag cagttttctg aagccagcca gcagatggca
121 gagctatccg aggtgttggt gctgaggctg gaaggctatg agaggcagca gaaggagatc
181 actcagctgc aggccgagat caccaagcta caacagcgtt gtcagtctta tggggcccag
241 acggagaaac tgcagcagca gctggcctca gagaagggag tccacccaga gagcctgcga
301 gctggctccc acatgcagga ttatggaagc aggcctcgtg aacgccagga ggatgggaag
361 agccatcgtc agcgttcc
```

HUNTINGTIN-ASSOCIATED PROTEIN-RELATED ASSAYS

The U.S. Government has a paid-up license in this invention and the right in limited circumstances to require the patent owner to license others on reasonable terms as provided for by the terms of grants awarded by the National Institutes of Health.

BACKGROUND OF THE INVENTION

Huntington's disease (HD) is an autosomal dominant neurodegenerative disorder caused by an expanding glutamine repeat in a gene termed IT15 or huntingtin[1]. Although this gene is widely expressed[2-9] and is required for normal development[10-12], the pathology of HD is restricted to the brain, for reasons that remain poorly understood. The huntingtin gene product is expressed at similar levels in patients and controls, and the genetics of the disorder[13,14] suggest that the expansion of the polyglutamine repeat induces a toxic gain of function, perhaps through interactions with other cellular proteins[15-18].

There is a need in the art for identification of the cellular components which are involved with huntingtin so that the disease can be better understood, diagnosed, and treated.

SUMMARY OF THE INVENTION

It is an object of the invention to provide a method for identifying compounds which interfere with the binding of huntingtin associated protein to huntingtin.

It is another object of the invention to provide methods for identifying compounds as candidate therapeutic agents.

It is an object of the invention to provide a method for identifying compounds which diminish the binding of huntingtin associated protein to huntingtin.

It is still another object of the invention to provide cells which can be used to identify compounds which interfere with the binding of huntingtin associated protein to huntingtin.

It is yet another object of the invention to provide a method for determining the quantity of human huntingtin which binds to human huntingtin associated protein, or of human huntingtin associated protein which binds to human huntingtin.

It is also an object of the invention to provide a method for screening for candidate drugs for treating, delaying onset, or preventing Huntington's Disease.

It is an object of the invention to provide a yeast cell useful in the screening of candidate drugs.

It is another object of the invention to provide cDNA segments encoding all or part of mammalian huntingtin associated proteins.

It is yet another object of the invention to provide fusion proteins comprising huntingtin associated proteins.

It is still another object of the invention to provide isolated mammalian proteins which are huntingtin associated proteins.

These and other objects of the invention are provided by one or more embodiments as described below. In one embodiment, a method for identifying compounds which interfere with the binding of huntingtin associated protein to huntingtin is provided. The compounds identified are candidate therapeutic agents. The method comprises the steps of:

contacting: a first protein; a second protein; and a compound to be tested for its capacity to interfere with binding of said first and second proteins to each other; wherein the first protein comprises huntingtin associated protein and the second protein comprises huntingtin or the first protein comprises huntingtin and the second protein comprises huntingtin associated protein; and determining the quantity of the first protein which is bound to, is displaced from, or is prevented from binding to, the second protein, wherein a compound which diminishes the quantity of the first protein bound to the second protein, or which displaces first protein bound to the second protein, or which prevents first protein from binding to the second protein, is identified as a candidate therapeutic agent.

In another embodiment, a second method for identifying compounds which interfere with the binding of huntingtin associated protein to huntingtin is provided. The identified compounds are candidate therapeutic agents. The method comprises the steps of:

contacting: a first polypeptide; a second polypeptide; and a compound to be tested for its capacity to interfere with binding of said first and second polypeptides to each other; wherein at least one of said first and said second polypeptides is a polypeptide which comprises less than all of the complete sequence of amino acids of huntingtin or huntingtin associated protein proteins, wherein each of said polypeptides contain a sufficient portion of huntingtin or huntingtin associated protein proteins to bind to the other polypeptide; wherein when said first polypeptide is huntingtin or a polypeptide which comprises less than all of the complete sequence of amino acids of huntingtin, then said second polypeptide is huntingtin associated protein or a polypeptide which comprises less than all of the complete sequence of amino acids of huntingtin associated protein; and when said first polypeptide is huntingtin associated protein or a polypeptide which comprises less than all of the complete sequence of amino acids of huntingtin associated protein, then said second polypeptide is huntingtin or a polypeptide which comprises less than all of the complete sequence of amino acids of huntingtin; and determining the quantity of the first polypeptide which is bound to, is displaced from, or is prevented from binding to, the second polypeptide, wherein a compound which diminishes the quantity of the first protein, or which prevents first protein from binding to the second protein, is identified as a candidate therapeutic agent.

In yet another embodiment of the invention a third method of identifying compounds which interfere with the binding of human huntingtin associated protein to human huntingtin is provided. The method comprises:

providing a cell which comprises three recombinant DNA constructs, said first construct encoding a first polypeptide fused to a sequence-specific DNA-binding domain, said second construct encoding a second polypeptide fused to a transcriptional activation domain, said third construct comprising a reporter gene downstream from a DNA element which is recognized by said sequence-specific DNA-binding domain, wherein said first polypeptide is a huntingtin associated protein polypeptide and said second protein is a huntingtin polypeptide, or said first polypeptide is a huntingtin polypeptide and said second polypeptide is a huntingtin associated protein polypeptide; wherein said polypeptides contain a sufficient portion of huntingtin and huntingtin associated protein proteins to bind to the other polypeptide;

contacting said cell with a compound to be tested for its capacity to inhibit binding of huntingtin to huntingtin associated protein;

determining the amount of expression of the reporter gene in the presence of said compound.

According to another embodiment a cell is provided for screening compounds. The cell comprises three recombinant DNA constructs, said first construct encoding a first polypeptide fused to a sequence-specific DNA-binding domain, said second construct encoding a second polypeptide fused to a transcriptional activation domain, said third construct comprising a reporter gene downstream from a DNA element which is recognized by said sequence-specific DNA-binding domain, wherein said first polypeptide is an huntingtin associated protein polypeptide and said second protein is a huntingtin polypeptide, or said first polypeptide is a huntingtin polypeptide and said second polypeptide is an huntingtin associated protein polypeptide; wherein said polypeptides contain a sufficient portion of huntingtin and huntingtin associated protein proteins to bind to the other polypeptide.

According to another embodiment a method is provided for determining the quantity of human huntingtin which binds to human huntingtin associated protein, or of human huntingtin associated protein which binds to human huntingtin. The method comprises:

contacting: a first protein and a second protein, wherein the first protein is human huntingtin associated protein and the second protein is human huntingtin or the first protein is human huntingtin and the second protein is human huntingtin associated protein; and determining the quantity of the first protein which is bound to the second protein.

In yet another embodiment of the invention, a method of screening for candidate drugs for treating, delaying onset, or preventing Huntington's Disease is provided. The method comprises the steps of:

contacting a compound to be tested with a yeast cell comprising: two fused gene constructs wherein a first construct comprises a yeast GAL-4 binding domain and a domain selected from the group consisting of: a glutamine repeat-containing domain of a huntingtin gene and a huntingtin binding domain of a huntingtin associated protein gene, and wherein a second construct comprises a yeast GAL-4 activation domain, and a domain selected from the group consisting of: a glutamine repeat-containing domain of a huntingtin gene and a huntingtin binding domain of a huntingtin associated protein gene, wherein when the first construct comprises a glutamine repeat-containing domain of a huntingtin gene, the second construct comprises a huntingtin binding domain of a huntingtin associated protein gene, and when the second construct comprises a glutamine repeat-containing domain of a huntingtin gene, the first construct comprises a huntingtin binding domain of a huntingtin associated protein gene; and a β-galactosidase reporter gene under the control of a yeast GAL-4 promoter, which is activated by the gene products of said two fused gene constructs, and selecting those compounds which diminish the expression of β-galactosidase by said cells.

In another embodiment of the invention a yeast cell is provided. The yeast cell comprises: two fused gene constructs and a β-galactosidase reporter gene under the control of a yeast GAL-4 promoter, wherein a first construct comprises a yeast GAL-4 binding domain and a domain selected from the group consisting of: a glutamine repeat-containing domain of a huntingtin gene and a huntingtin binding domain of a huntingtin associated protein gene, and a second construct comprises a yeast GAL-4 activation domain, and a domain selected from the group consisting of: a glutamine repeat-containing domain of a huntingtin gene and a huntingtin binding domain of a huntingtin associated protein gene, wherein when the first construct comprises a glutamine repeat-containing domain of a huntingtin gene, the second construct comprises a huntingtin binding domain of a huntingtin associated protein gene, and when the second construct comprises a glutamine repeat-containing domain of a huntingtin gene, the first construct comprises a huntingtin binding domain of a huntingtin associated protein gene; and said β-galactosidase reporter gene is activated by the gene products of said two fused gene constructs.

According to still another embodiment of the invention a cDNA segment is provided. The cDNA segment encodes at least 8, 12, or preferably 15 contiguous amino acids of a mammalian huntingtin associated protein.

In yet another embodiment of the invention a cDNA segment is provided which consists of at least 20 or preferably 30 or 40 contiguous nucleotides of a mammalian gene encoding huntingtin associated protein.

In another embodiment of the invention a fusion protein is provided. It consists of all or a portion of a first and a second protein, wherein said second protein is a mammalian huntingtin associated protein, and the portion of said mammalian huntingtin associated protein is sufficient to bind to huntingtin.

In still another embodiment of the invention an isolated mammalian protein is provided. It is a huntington associated protein.

These and other embodiments of the invention provide the art with techniques and tools for identifying drugs for the amelioration of Huntington's Disease.

BRIEF DESCRIPTION OF THE DRAWINGS

(FIG. 1*a*) Filter assays for β-galactosidase activity in transformed yeast with proteins fused to the GAL-4 binding domain (BD) and the activation domain(AD) (BD construct+AD construct). HAP1: AD construct of rHAP1. Only co-expression of rHAP1 plus the N-terminal portions of huntingtin containing either 23 or 44 glutamine repeats (HD23Q or HD44Q) activate the β-galactosidase reporter gene (blue). Co-transformation with c-Fos and c-Jun (Fos+Jun) served as the positive control. (FIG. 1*b*) Liquid assays of interactions of rHAP1 with various proteins in yeast cells. Atrophin (21Q) is the GAL-4 binding domain construct containing 263 amino acids of atrophin-1 with 21 glutamine repeats. (FIG. 1*c*) Coomassie blue staining of GST-ENAC, GST and GST-HAP1 (rHAP1) fusion proteins. ENAC is the N-terminal portion (107 amino acids) of a subunit of the amiloride-sensitive sodium channel expressed predominately in colon, kidney and tongue but not in brain[24,25]. (FIG. 1*d*) Western blot analysis of huntingtins from 293 cells transfected with an HD cDNA using anti-peptide antibody for the huntingtin (AP-81)[4]. (FIG. 1*e*) Binding of GST-HAP1 to huntingtins in transfected 293 cells. (FIG. 1*f*) Inputs of huntingtins from lymphoblasts with 22/19; 44/20; and 82/19 glutamine repeats, respectively, were reacted with the GST-HAP1 fusion protein and Western blot (FIG. 1*g*) reveals the amount of huntingtin bound to GST-HAP1.

FIGS. 2*a*–2*c*. Schematic diagram and deduced amino acid sequences of HAP1 (SEQ ID NO:22) and HLP1 (SEQ ID NO:25). (FIG. 2*a*) The open reading frame is indicated as a box. A black box corresponds to the region of rHAP1 cDNA isolated from the yeast two hybrid screening. rHAP1-A and rHAP1-B were isolated from rat brain cDNA libraries and have identical sequences in their overlapping regions, with different amino acids in the C-terminus (shown by shaded boxes at the C-terminus). An acidic amino acid rich region is indicated as a shaded box. rHAP1-A contains the entire translated region, while rHAP1-B contains the same sequence of the untranslated region on the end 3'. The region of partial cDNA of human HLP1 (SEQ ID NO:9) or HAP1 (SEQ ID NO:13) isolated by RT-PCR are also shown. (FIG. 2*b*) The first ATG in rHAP1-A (SEQ ID NO:10) is used as a putative start codon and deduced amino acid sequences of rHAP1-A (SEQ ID NO:22) and rHAP1-B (SEQ ID NO:23) are shown. The acidic amino acid rich region is underlined and the original sequence of rHAP1 isolated from the yeast two hybrid system is in the bold type. (FIG. 2*c*) Alignment of partial human HLP1 (SEQ ID NO:25) and HAP1 (SEQ ID NO:24) amino acid sequences with rHAP1A (SEQ ID NO:22). Amino acid sequences derived from PCR primers are underlined. Amino acid residues identical to rHAP1 are indicated with vertical lines.

FIGS. **3*a*–3*c*. Expression of HAP1.

Figure 1A:
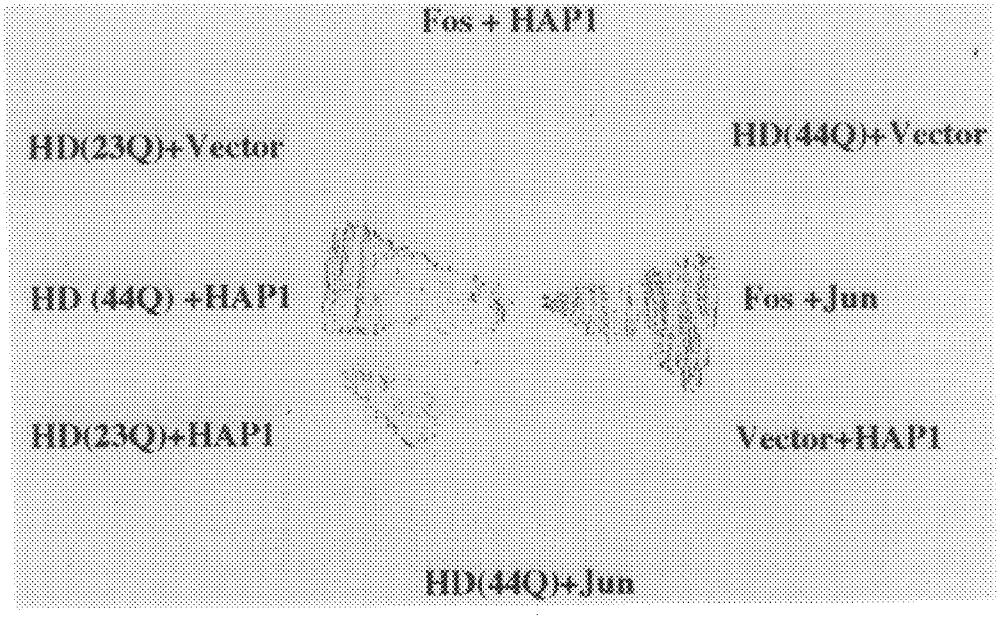
FIGS. 1*a*–1*g*: Association of rat HAP1 with huntingtin.

FIGS. **4*a*–4*b*. Co-immunoprecipitation of (FIG. 4*a*) transfected rHAP1-A and endogenous human huntingtins in HEK 293 cells and (FIG. 4*b***) endogenous rat HAP1 and huntingtins. 293 cells: untransfected cells; Lysates: cell extracts from transfected 293 cells with rHAP1-A cDNA; AP81: with purified antibody (AP-81) for huntingtin; $IP_3R$-1: with antibody for $IP_3$ receptor type 1; AP81+peptide: with AP81 preabsorbed with the peptide immunogen. HAP1-Ab, rat HAP1 antibodies.

FIG. **5*a*–1 to 5*a*–3, 5*b*–1 to 5*b*–3, and 5*c*–1 to 5*c*–3. The rat HAP1-A (FIG. 5*a*–2 to 5*b*–1) (SEQ ID NO:10), rat HAP1-B (FIG. 5*b*–2 to 5*c*–1) (SEQ ID NO:11), human HLP (FIG. 5*c*–1) (SEQ ID NO:9) and human HAP1 (FIG. 5*c*–2) (SEQ ID NO:12) nucleotide coding sequences are shown. The amino acid translation of rat HAP1-A (SEQ ID NO:22) is also shown in FIG. 5*a*–1**.

DETAILED DESCRIPTION OF THE PREFERRED EMBODIMENTS

It is a finding of the present inventors that huntingtin associated protein (HAP1) binds to the protein product of mammalian Huntington's Disease loci, termed herein, huntingtin. The binding is enhanced by an expanded polyglutamine repeat in huntingtin, the length of which is also known to correlate with the time of disease onset[19-21]. In addition, HAP1 protein, in contrast to huntingtin itself, is expressed selectively in the brain.

The normal function of huntingtin is unknown, though it has been proposed to play a role in microtubule mediated transport or vesicle function[7,9]. The selective expression of HAP1 in brain, in contrast to the ubiquitous distribution of HD gene expression, suggests that HAP1 may contribute to the brain-specific pathology of HD. The pathology of HD involves most or all of the brain in advanced cases, though some regions show striking early selective vulnerability. Though rat HAP1 (rHAP1) is highly expressed in many regions of rat brain, the message for human HAP1 (hHAP1) can be detected most consistently by RT-PCR in the human brain regions (caudate and cortex) that are most affected in HD. Thus, the levels of expression of human HAP1 in specific cell populations may influence their vulnerability.

The screening methods of the present invention all rely on the principle of interference in the binding of huntingtin and huntingtin associated protein by a compound. Thus any assay format for measuring protein—protein interactions that is known in the art can profitably be used. For example, both in vitro and in vivo tests can be used. One of the proteins can be immobilized, for example, on a microtiter dish, or on a column packing matrix. Immobilization can be direct or indirect, e.g., through a domain of a fused protein. Assays can employ radiolabels, enzyme assays, antibodies, florescent labels, etc. Binding interactions can be assessed by measuring the bound or the unbound fraction.

According to some embodiments of the invention, the entire huntingtin or huntingtin associated protein is used, as is, or fused to another polypeptide domain or protein. Alternatively, polypeptide portions of either huntingtin or huntingtin associated protein can be used, so long as they contain the portions of huntingtin and huntingtin associated protein which are required for binding to each other. Suitable portions of human huntingtin associated protein (SEQ ID NO:24) for use include amino acids 105–136, 4–136, 50–136, and 75–136. Suitable portions of huntingtin (SEQ ID NO:21) for use include amino acids 1–230 and 1–930, although the minimal amount has not been determined. It is believed that the glutamine repeat units are necessary for binding, however, flanking amino acids may also be necessary for proper binding conformation and/or specificity.

In vivo assays such as the GAL4 based assays described by Fields et al.[28] can be used. Such assays employ fusion proteins of the two interacting proteins of interest. One partner is fused to an activation domain and one partner is fused to a DNA binding domain. Neither domain by itself will activate transcription of a suitable reporter gene. However, when the two domains are brought into proximity, such as by the interaction of the two interacting proteins, then the reporter's transcription is activated. Other suitable systems have been developed. Spencer et al. *Science*, 262, 1019–1024 (1993) developed a system which relies on the interaction of FKBP12 and FK1012. Fearon et al., *Proc. Natl. Acad. Sci. USA*, 89,7958–7962 (1992) teaches a system which is based on yeast GAL4 but which can be used in mammalian cells. Reporter genes which are used are preferably those whose expression can be quantitatively or semi-quantitatively assayed, including drug resistance enzymes and anabolic enzymes. Both the his3 and the β-galactosidase genes can be used to advantage.

In vivo assays may be preferable to in vitro assays because they require that the compound being tested penetrate the cells and locate the appropriate target proteins. However, both types of methods may be used, either individually or sequentially.

Candidate drugs are identified as those which inhibit the binding of huntingtin to huntingtin associated protein. Such inhibitory molecules can be identified by screening for interference of the huntingtin/huntingtin associated protein interaction where one of the binding partners is bound to a solid support and the other partner is labeled. Antibodies specific for epitopes on huntingtin or huntingtin associated protein which are involved in the binding interaction will interfere with such binding. Solid supports which may be used include any polymers which are known to bind proteins. The support may be in the form of a filter, column packing matrix, beads, microtiter dish, and the like. Labeling of proteins can be accomplished according to any technique known in the art. Radiolabels, enzymatic labels, and fluorescent labels can be used advantageously. Alternatively, both huntingtin and huntingtin associated protein may be in solution and bound molecules separated from unbound subsequently. Any separation technique known in the art may be employed, including immunoprecipitation or immunoaffinity separation with an antibody specific for the unlabeled binding partner.

It has been found that amino acid residues 1–230 of huntingtin (SEQ ID NO:21) are sufficient for the interaction of huntingtin and huntingtin associated protein. However, some of these residues may not be necessary for binding. In addition, it has been found that residues 1–136 of human huntingtin associated protein (SEQ ID NO:24) are sufficient for binding to huntingtin. Again, less may be required. Loss of residues corresponding to residues 105–136 leads to non-binding proteins, as demonstrated by hHLP1. Thus it is presumed that some of the amino acids in the 105–136 region are necessary. Additional residues in the 1–105 region may also be required.

According to another aspect of the invention, the binding of huntingtin and huntingtin associated protein can be quantitatively evaluated in the absence of test compounds. Such assays can be used to determine if a biological sample contains a mutant huntingtin protein. Such assays can also be used to determine if a particular tissue expresses huntingtin associated proteins.

cDNA molecules and segments are also provided by the present invention. A segment may, for example, be covalently joined to a vector or to another gene. The cDNA molecules and segments of the present invention are those which encode huntingtin associated proteins. Preferably they encode at least 12 contiguous amino acids of a mammalian huntingtin associated protein. In some instances, such as in the preparation of gene primers and probes, the use of a segment consisting of as little as 17, 20, 25, or 30 nucleotides may be sufficient to obtain specific binding. Such segments may also be sufficient to encode epitopes useful in the generation of antibodies which specifically bind to huntingtin associated proteins. Immunization of experimental animals to generate polyclonal antisera is well-known in the art. Manipulation of such immunized animals to obtain monoclonal antisera is also well-known and contemplated by the invention.

Huntingtin associated proteins are also contemplated by the present invention. Such proteins may be the full-length protein, as found in vivo, or may be portions of the protein which can be used as polypeptide immunogens, or fused to other protein domains. The full-length proteins of the present invention are isolated from other cellular components, such as DNA, RNA, lipids, and often other proteins. Fusion proteins can be made, as are known in the art, using recombinant DNA techniques and expression of fused genes in cells.

EXAMPLE

Example 1

This example demonstrates the isolation of the gene encoding huntingtin associated protein from rat.

Figure 1B:
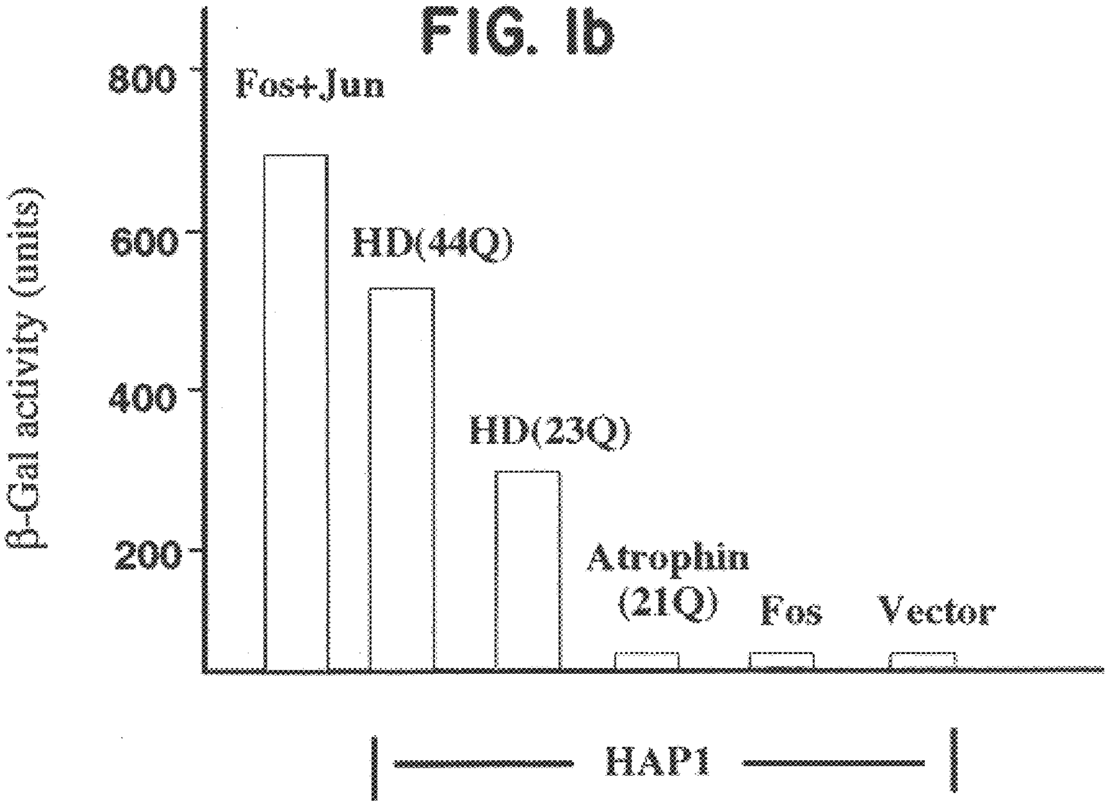

A cDNA encoding the first 230 amino acids of huntingtin containing 44 glutamine repeats was ligated to the GAL-4 binding domain in plasmid vector pPC97 for yeast two hybrid screening with a rat brain cDNA library. This region was chosen because it includes the portion of the protein in which a glutamine repeat is expanded in HD[1]. Overall, longer expansions are associated with earlier age of onset. Alleles with 44 repeats are among the most common in the expanded range, and can cause onset of the disorder at ages ranging from the 20s to the 60s19-21. Screening of approximately 100,000 colonies resulted in one positive clone. This clone (rHAP1-BR, rat huntingtin Associated Proteinl Binding Region) had an insert of 507 base pairs with no homology to known genes. Co-transformation of yeast with rHAP1 plus the HD constructs resulted in blue colonies which were not evident following co-transformation with either vector alone or with unrelated fusion proteins in either vector (FIG. 1*a*). The interaction was positive using the HD fusion protein containing either a normal repeat length (23 glutamines) or an expanded repeat (44 glutamines). The interaction of rHAP1 with huntingtin was stronger with the 44 glutamine repeats than with the 23 repeats using a semi-quantitative liquid assay (FIG. 1*b*). To determine whether the interaction is specific to huntingtin or would be positive for another protein with a polyglutamine tract, we performed a similar experiment using rHAP1 plus an atrophin-1 construct, which contains a 21 glutamine repeat[22]. This showed no evidence for interaction in either filter or liquid assays.

Methods: The partial length of HD cDNAs were isolated from a human brain cortex cDNA library (Stratagene) using a CAG repeat oligonucleotide probe[16] or PCR with the first strand cDNA from a HD brain tissue. A cDNA construct containing the first 230 amino acids with 44 or 23 glutamine repeats was in-frame fused with the GAL4 DNA binding domain of plasmid pPC97[27]. An adult rat hippocampus cDNA library was constructed using plasmid pPC86 containing the GAL4 activation domain. Transformations of a yeast strain PCY2 and filter assays of β-galactosidase activity were performed according to the methods described previously[27] and the controls were included as described by Fields[28]. The liquid assay to quantify β-galactosidase activity is as previously described[29].

Example 2

This example demonstrates an in vitro binding assay using huntingtin and huntingtin associated protein fusion proteins. It also demonstrates the correlation between strength of binding and number of glutamine repeats in the huntingtin protein. In addition, it demonstrates that rat huntingtin associated protein binds to human huntingtin.

Figures 1C, 1D, 1E, 1F, 1G:
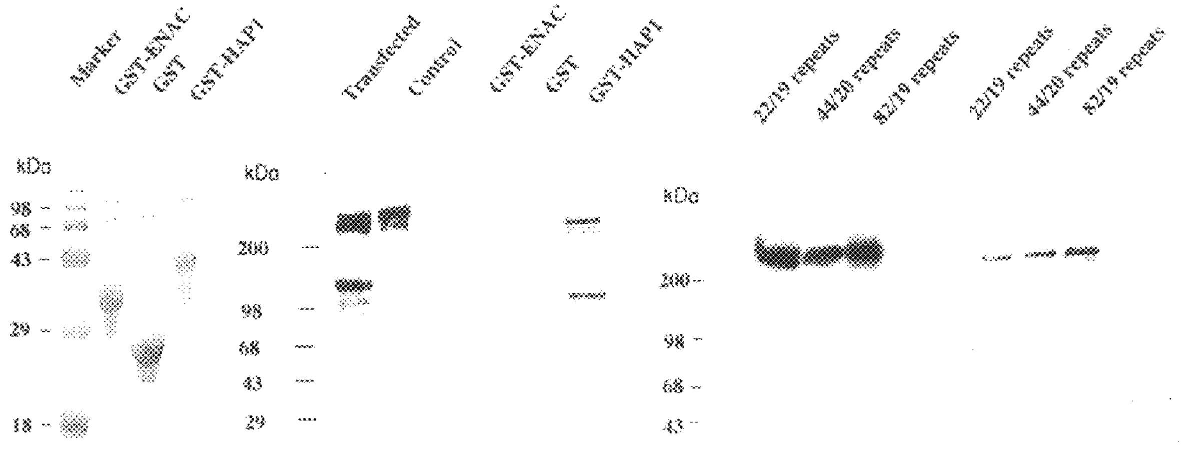

In vitro binding assays were then performed using glutathione-S-transferase (GST) fusion proteins (FIG. 1*c*). An HD cDNA encoding the N-terminal region (930 amino acids with 44 repeats) was fused in frame to an expression vector pEBVHIS (Invitrogen). Transfection of this construct into HEK-293 cells resulted in a band (131 kDa) that was recognized by a huntingtin specific antibody[4] (FIG. 1*d*). The endogenous protein (350 kDa) could be seen as well. When an extract from cells transfected with the N-terminal huntingtin construct was incubated with GST-HAP1 protein linked to agarose beads, both the native huntingtin and the transfected huntingtin with the expanded repeat (44 glutamines) were specifically retained on the beads (FIGS. 1*c*, 1*d*, 1*e*). A similar experiment was performed using lymphoblastoid cell lines from a normal individual and HD patients with varying lengths of glutamine repeats (FIG. 1*f*). Cell extracts containing the huntingtin with 82 repeats yielded the strongest binding compared to the huntingtin with 44 repeats, and both proteins showed increased binding to GST-HAP1 compared to the protein from the normal individual (19–22 repeats) (FIG. 1*g*). Alleles of ≧70 repeats are in the severely expanded range and nearly always cause HD with juvenile onset.

Methods: rHAP1 cDNA (507 bp) isolated from the yeast two hybrid screening was inserted into pGEX-2T vector (Pharmacia) and GST fusion protein expression and purification were essentially as previously described[30]. The sources containing huntingtins were 293 cells transfected with the cDNA encoding the partial N-terminal portion (930 amino acids with 44 glutamine repeats) of huntingtin fused in frame to pEBVHIS vector (Invitrogen) and transformed lymphocytes (lymphoblast) from a normal individual and HD patients. The 293 cells from a 10 cm dish or 100 ml lymphoblast cultures were lysed in 1.5 ml binding buffer (1% Triton, 160 mM NaCl, 50 mM Hepes (pH 7.4), 2.5 mM MgCl, 1.5 mM CaCl and 2.5 mM KCl, 1 mM PMSF, and 2 μg/ml each of pepstatin, leupeptin and aprotinin). Cell lysates were pre-incubated with agarose beads containing about 0.5–1 mg GST protein at 4° C. for 30 min, clarified by centrifugation at 10,000×g for 10 min at 4° C., then incubated with agarose beads containing 0.5 μg GST-HAP1 or other fusion proteins at 4° C. for 1 hr. Agarose beads were washed three times with 1 ml binding buffer. Proteins eluted from beads with SDS-sample buffer were detected in Western blot analysis with huntingtin antibodies AP-81.

Example 3

This example demonstrates the cloning of two full-length cDNAs encoding huntingtin associated protein.

Figure 2A:
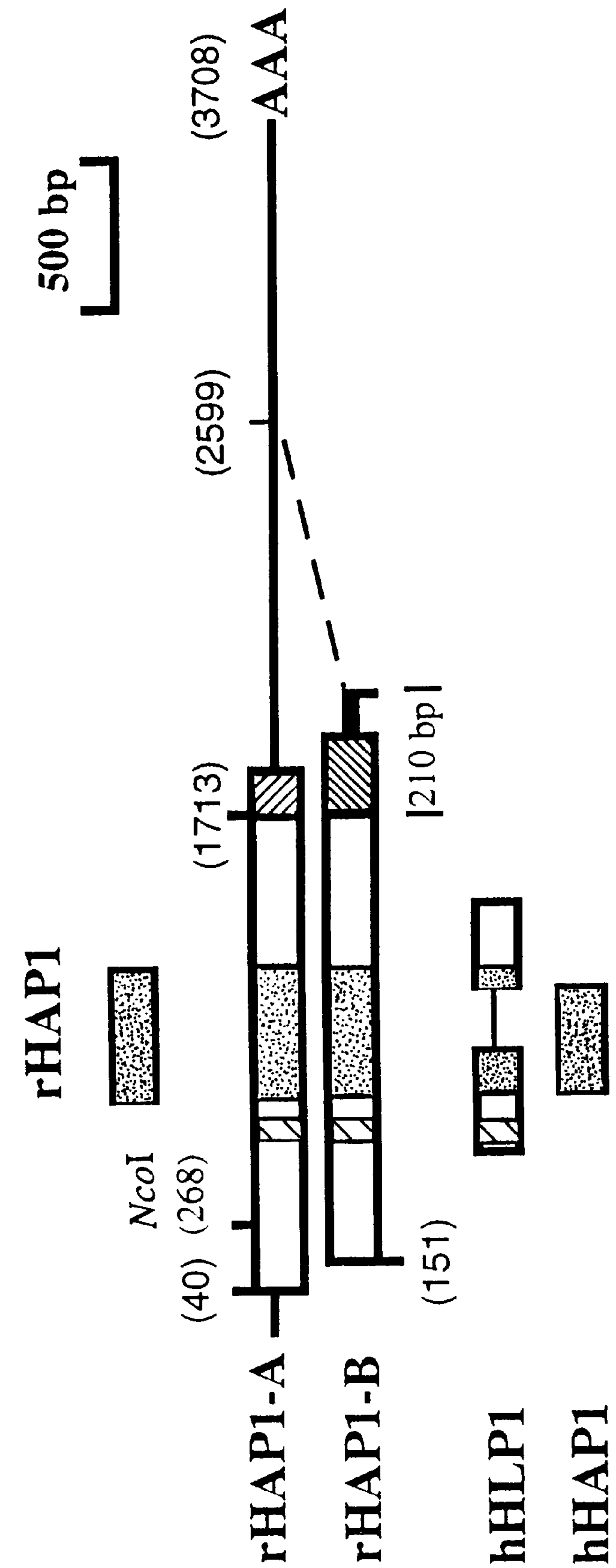

The cDNA insert from the rHAP1 clone was used to screen rat brain cDNA libraries to obtain a full length cDNA sequence. rHAP1-A and rHAP1-B represent two groups of cDNAs that display different sequences in the C-terminal region (FIGS. 2*a*, 2*b*). There are no significant homologies to known genes in the database. Both proteins are highly hydrophilic with no hydrophobic region. Their calculated PI value is about 4.67 with a high percentage of charged amino acids, including a glutamate and aspartate rich region ($Asp^{217}$–$Asp^{237}$).

Methods: The cDNA for rat HAP1 (507 bp) isolated from the yeast two hybrid screening was labeled with $^{32}P$ as a probe to screen rat brain cDNA libraries (Stratagene). rHAP1-A and rHAP1-B represent two groups of cDNA (from a total of 30) with different sequences at the C-terminus. Six cDNAs have been sequenced on both strands and amino acid sequences of rHAP1-A and rHAP1-B are shown.

Example 4

This example demonstrates the isolation of genes related to huntingtin associated protein from human. The encoded proteins do not bind to huntingtin.

We then used a PCR approach to identify hHAP1 from human caudate tissue, with a variety of primers based on the sequences of both ends of putative binding region (rHAP1). Six types of subclones of PCR products contain 5' and 3' regions with about 70% amino acid identity to rHAP1, but display different deletions or insertions in the region corresponding to the midportion of rHAP1. These cDNAs are termed hHLP (human HAP-like protein) because they all lack the midportion of rHAP1 (between $^{371}$Gly and $^{421}$Asp) (FIG. 2*c*) and were unable to generate blue colonies when introduced into yeast with HD cDNA.

Methods: RT-PCR with human caudate RNA was performed to identify human HLP cDNA. hHLP1 was isolated with the sense primer gatgatctccttcagctctac (SEQ ID NO:3) (DDLLQLY) (SEQ ID NO:14) and antisense primer ccagttggacagttgctggaggac (SEQ ID NO:2) (VLQQLS). cDNA products were then subeloned and sequenced.

Example 5

This example demonstrates the isolation of a cDNA fragment from human caudate tissue which is highly homologous to rat huntingtin associated protein and which binds to huntingtin.

We obtained a cDNA fragment from human caudate tissue, which contains 94% nucleic acid identity (375 bp) to rHAP1 with 96% amino acid identity and is termed hHAP1 (human HAP1, FIG. 2*c*). Co-transformation of yeast with hHAP1 cDNA plus the HD constructs (44 or 23 repeats) produced blue colonies with similar intensity to those with rHAP1 cDNA (data not shown), indicating that the midportion of HAP1 is crucial for interactions with the HD protein. Southern analysis using human genomic DNA is consistent with the existence of at least two separate genes related to rHAP1 (data not shown).

Methods: The sense oligonucleotide primer accactgcccacagctggaag (SEQ ID NO:3) and the antisense primer catagtgggtgacagaacct (SEQ ID NO:4) that correspond to rHAP1 amino acid sequence HCPQLE (SEQ ID NO:16) and GSVTHY (SEQ ID NO:17) respectively, were used to amplify human caudate cDNA at 95° C. for 1 min, 55° C. for 1 min then 72° C. for 1 min for 30 cycles. cDNA were amplified again using the sense primer agcagaagctgaagctgctgga (SEQ ID NO:5) and antisense primer agaacctgcaggcattgagg (SEQ ID NO:6) that encode amino acid sequences KLKLLE (SEQ ID NO:18) and SMPAGS (SEQ ID NO:19) respectively, under the same PCR condition.

Example 6

This example demonstrates that mRNA encoding huntingtin associated protein is highly expressed in the brain, but not in several peripheral tissues.

Figure 3A:
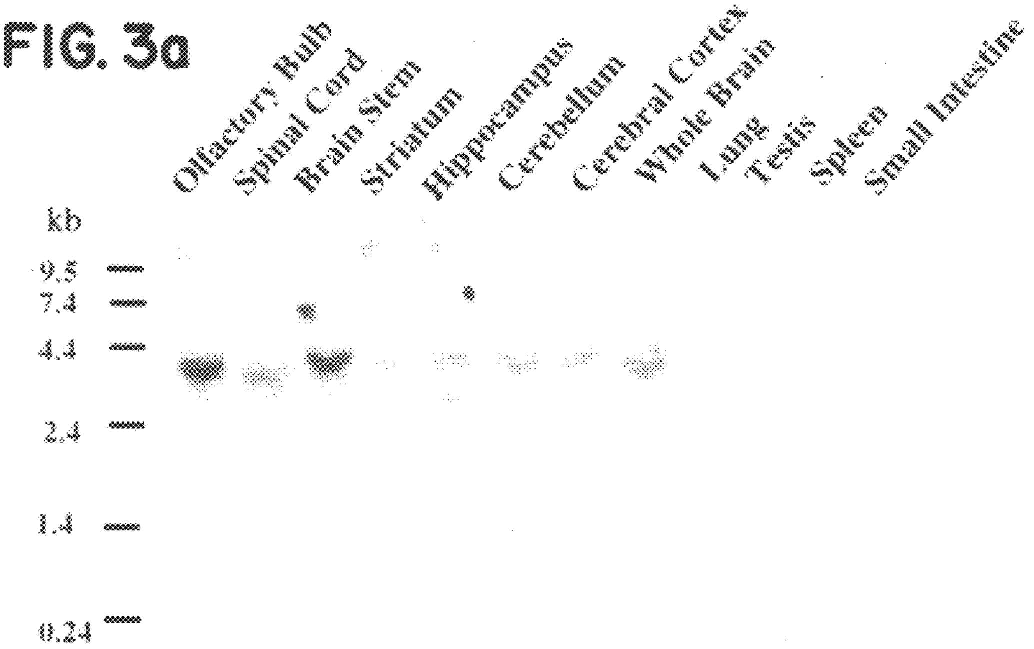
(FIG. 3*a*) Northern blot analysis of rat HAP-1 mRNA (FIG. 3*b*) and RT-PCR analysis of expression of human HAP1 using primers spanning the binding region. St.N.: subthalamic nucleus, Cd.: Caudate, Ctx. Cerebral cortex, Hip.: Hippocampus, Cereb.: cerebellum, Genomic: human genomic DNA, dH2O.: no RNA input. hHAP1: hHAP1 plasmid cDNA.
Figure 3B:
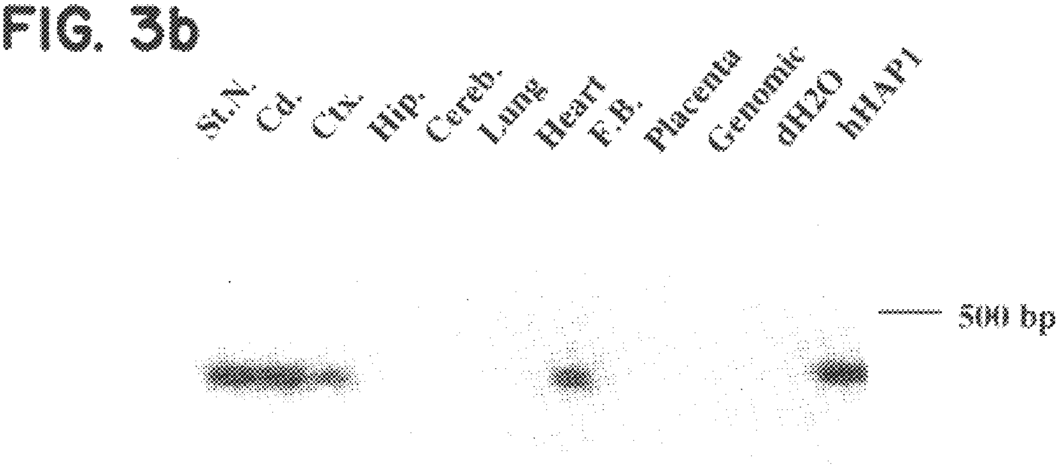
(FIG. 3*c***) Immunoblot analysis of HAP1 protein. Human Ctx: Human cerebral Cortex.

Northern blot analysis of the expression of the rHAP1 (FIG. 3*a*) shows transcripts of approximately 4.0 kb in rat brain, with the suggestion of two partially resolved bands. Expression is high in many brain regions. By contrast there is no detectable signal in several peripheral tissues (FIG. 3*a*). To confirm the expression of hHAP1 in human brain, we conducted RT-PCR analysis with primers derived from hHAP1 (FIG. 3*b*). We obtained PCR products with the expected size (320 bp), that could be detected by hybridization with a hHAP1 cDNA probe. This form is detected in subthalamic nucleus, caudate, cerebral cortex, and fetal brain.

Methods: Twenty μg total RNA from each tissue and the $^{32}P$ labeled cDNA probe of rHAP1 were used in Northern blot analysis and the blot was exposed to X-ray film for 24 hr. For the human RT-PCR analysis (FIG. 3*b*), PCR products obtained using the sense primer atgctcattctggagtgtgtg (SEQ ID NO:7) (MLILECV) (SEQ ID NO:20) and antisense primer agaacctgcaggcattgagg (SEQ ID NO:8) (SMPAGS) (SEQ ID NO:19) at an annealing temperature 62° C. for 35 cycles were separated on 1% agarose gel, transferred onto a nitrocellulose membrane and hybridized with the $^{32}P$ labeled cDNA probe of hHAP1 under a high stringency conditions. One of five independent RT-PCR assays with commercial human cDNA (Clontech) or our synthesized cDNA is shown in (FIG. 3*b*). This experiment is representative, but other experiments did yield a detectable band in other brain regions such as hippocampus (Hip).

Example 7

This example demonstrates that huntingtin associated protein is expressed in the brain but not in peripheral tissues, confirming the findings with mRNA expression.

Figure 3C:

Affinity purified antibodies raised against GST-HAP1 were used to confirm expression of the rHAP1 protein. A construct containing the full length protein of rHAP1-A or rHAP1-B was transfected into HEK-293 cells. Western blots of rat whole brain contain three immunoreactive bands (FIG. 3*c*). The middle band is the same molecular mass as the transfected rHAP1-A protein (75 kDa) in 293 cells. In vitro translation of rHAP1-A cDNA also yields a product of the same apparent molecular weight (75 kDa, data not shown). The upper band (85 kDa) corresponds to the transfected rHAP1-B. The lowest, 68–70 kDa, is the size predicted for rHAP1-A or rHAP1-B cDNA and is present in both rat and human brain. By contrast, several peripheral tissues from rat and human showed no immunoreactivity (FIG. 3*c*). The immunoreactivity of all three bands could be eliminated by preabsorption of antibodies with the antigen (data not shown). The three bands in the rat brain might reflect alternative splicing, which would fit with the existence of two distinct cDNA sequences for rHAP1. The variety of HAP cDNA homologues obtained by PCR suggests the existence of multiple human HAP1 or HAP-like proteins (HLP). Antibodies for rHAP1 might be unable to distinguish them because of their similar mobilities in the gel or different expression levels. Post-translational modification may also play a role and fit with the molecular weights of the upper two bands being greater than the predicted molecular weights.

Methods: For the Western blots (FIG. 3*c*), tissues were homogenized in PBS buffer with protease inhibitors as described in FIG. 2 and about 75 mg proteins were used in Western blot except for transfected cells (1 μg). HEK-293 cells were transfected with a pCIS-2 expression vector (Genentech) containing a rat HAP1 cDNA construct using the $Ca^{++}$-phosphate precipitation method. The N-terminal sequence of rHAP1-A was inserted into rHAP1-B using the Nco I restriction site to generate the full length protein of rHAP1-B. The GST-HAP1 fusion protein was used as an antigen for production of antiserum from rabbits (HRP Inc.). The antiserum (1.5 ml) was incubated with 20 mg GST-HAP1 antigen transferred onto the nitrocellulose. The nitrocellulose was washed with PBS, and antibodies were eluted with 1 ml 100 mM glycine (pH 2.8). The elution fluid was dialyzed against PBS overnight. Purified antiserum (1:2000) or preabsorbed antiserum in PBS containing 3% BSA was used for Western blot analysis with an enhanced chemiluminescence kit (Amersham).

Example 8

This example demonstrates that, like the portion of huntingtin associated protein, full-length huntingtin associated protein interacts with huntingtin in vivo.

Figure 4A:
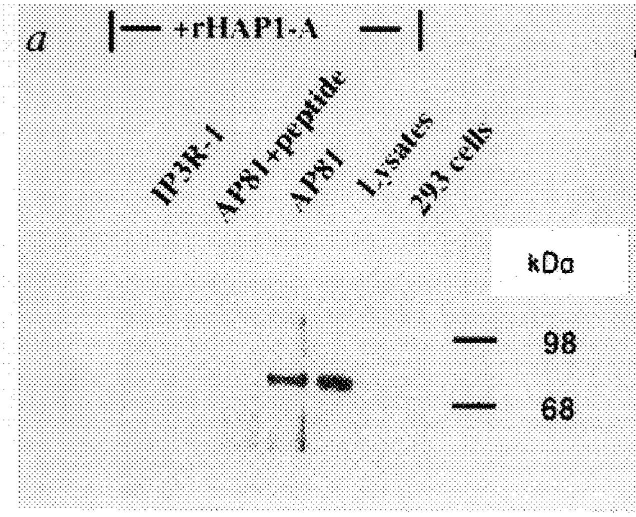
Figure 4B:
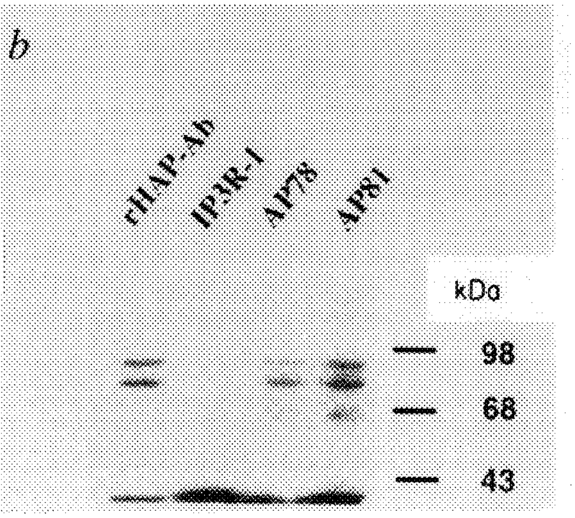

To confirm that the full length rHAP1 interacts with huntingtin in vivo, we conducted co-immunoprecipitation experiments. rHAP1-A protein transfected in 293 cells could be precipitated specifically with affinity purified antibody to huntingtin, AP81, and this precipitation could be blocked by the peptide antigen (FIG. 4*a*). Using a different peptide antibody for huntingtin (AP78), we obtained similar results (data not shown). Using whole rat brain, we also observed coprecipitation of both rat HAP1 and huntingtins with AP78 or AP81 (FIG. 4*b*). We have not yet clearly shown co-immunoprecipitation from human brain tissue, which may reflect the complex mixture of hHAP1 and HLPs and their possibly different tissue localization. Another factor may be the difficulty of using human postmortem brain tissues.

The yeast two hybrid assays and the in vitro binding data show that the association between HAP1 and huntingtin is enhanced by increasing lengths of the glutamine repeat. Binding may be influenced by the flanking amino acids, since there is no binding to the atrophin-1 protein which contains essentially the same number of glutamines (21) as the HD construct (23 glutamines). The affinity of the interaction may be increased by an altered conformation of the huntingtin due to the expanded glutamine repeat. The enhanced association of HAP1 with a huntingtin containing an expanded polyglutamine repeat could contribute to the pathophysiology of HD, consistent with the toxic gain of function hypothesis.

Methods: Transfected cells with rHAP1-A cDNA from a 10 cm plate or whole rat brain (0.15 g/wt) were lysed in 1.5 ml binding buffer as for GST fusion protein binding experiments, and 750 ml lysate was incubated with 100 ml antibodies linked beads (50% slurry) at 4° C. for 1 hr. Affinity purified antibodies (AP-78 or AP81, 20 mg) were coupled to 1 ml protein-A agarose beads using 100 mM dimethyl pimelimidate. AP81 linked beads pre-absorbed with peptide immunogen (20 μg/ml) overnight or antibodies linked beads for IP3 receptor type-3 were used as the controls. Proteins were eluted from beads with 100 mM glycine (pH 2.8) following washes with the binding buffer and eluted proteins were detected on Western blots with purified rHAP1 antibodies (1:2000).

References

1. Huntington's Disease Collaborative Research Group. *Cell* 72, 971–983 (1993)
2. Li, S-H., et al. *Neuron* 11, 985–993 (1993)
3. Strong, T. V., et al. *Nature Genet*. 5, 259–265 (1993)
4. Sharp, A. H., et al. *Neuron* 14, 1065–1074 (1995)
5. Schilling, G., et al. *Hum. Mol. Genet*. 4, 1365–1371 (1995)
6. Trottier, Y., et al. *Nature Genet*. 10, 104–110 (1995)
7. DiFiglia, M., et al. *Neuron* 14 1075–1081 (1995)
8. Persichetti, F., et al. *Mol. Med*. 1, 374–383 (1995)
9. Gutekunst, C.-A., et al. *Proc. Natl. Acad. Sci*., in press
10. Nasir, J., Florescoet al. *Cell* 81, 811–823 (1995).
11. Duyao, M. P., et al. *Science* 269, 407–410 (1995)
12. Zeitlin, S., Liu, J.-P., Chapman, D. L., Papaioannou, V. E., and Efstrtiatis, A., *Nature Genet*. 10, in press
13. Wexler, N. S., et al. *Nature* 326, 194–197 (1987)
14. Ambrose, C. M., et al. *Somat. Cell Mol. Genet*. 20, 27–38 (1995)
15. Gusella, J. F., MacDonald, M. E., Ambrose, C. M. and Duyao, M. P. *Arch. Neurol*. 50, 1157–1163 (1993)
16. Ross, C. A., McInnis, M. G., Margolis, R. L., Antonarakis, S. E. and Li, S-H. *Trends Neurosci*. 16, 254–260 (1993)
17. Albin, R. L., and Tagle, D. A. *Trends Neurosci*. 18, 11–14 (1995)
18. Ross, C. A. *Neuron* 15, 493–496, (1995)
19. Duyao, M, et al. *Nature Genetics* 4, 387–392 (1993)
20. Andrew, S. E., et al. *Nature Genet*. 4, 398–403 (1993)
21. Stine, O. C., et al. *Hum. Mol. Genet*. 2, 1547–1549 (1993)
22. Margolis, R. L., Li, S-H. and Ross, C. A. *Mol. Brain Res*. in press, (1995)
23. Beal, M. F. *Ann. Neurol*. 38, 357–366 (1995)
24. Canessa, C. M., Horisberger, J. D. and Rossier, B. C. *Nature* 361, 467–470. (1993)

25. Li, X. J., Blackshaw, S. and Snyder, S. H. *Proc. Natl. Acad. Sci. USA* 91, 1814–1818 (1994)

26. Li, S-H., McInnis, M. G., Margolis, R. L., Antonarakis, S. E. and Ross, C. A. *Genomics* 16, 572–579 (1993)

27. Chevray, P. M. and Nathans, D. *Proc Natl. Acad. Sci. USA* 89, 5789–5793 (1992)

28. Fields, S. and Stemglanz, R. *Trends Genet* 10, 286–292 (1994)

29. Guarente, L. *Methods Enzymol.* 101, 181–91 (1983)

30. Guan, K. and Dixon, J. E. *Ann. Biochem.* 192, 262–267 (1991)

We claim:

1. A method for identifying compounds which interfere with the binding of huntingtin associated protein-1 (HAP1) to huntingtin, said compounds being candidate therapeutic agents, said method comprising the steps of:

contacting: a first protein; a second protein; and a compound to be tested for its capacity to interfere with binding of said first and second proteins to each other; wherein the first protein comprises huntingtin as shown in SEQ ID NO:21 and the second protein comprises huntingtin associated protein-1 (HAP1), as shown in SEQ ID NO:22, 23, or 24 and determining a quantity of the first protein or the second protein, wherein a compound which diminishes the quantity of the first protein bound to the second protein when compared to control values is identified as a candidate therapeutic agent.

2. The method of claim 1 wherein an antibody is used to determine the quantity of the first protein or the second protein.

3. The method of claim 2 wherein an antibody specifically immunoreactive with said first protein or said second protein is used to immunoprecipitate bound complexes of said first protein and said second protein.

4. The method of claim 1 wherein one of said first protein and said second protein is fixed to a solid support.

5. The method of claim 1 wherein one of said first protein and said second protein is labeled.

6. The method of claim 1 wherein at least one of said first protein and said second protein is a fusion protein.

7. The method of claim 1 wherein said second protein consists of huntingtin associated protein-1 (HAP1) as shown in SEQ ID NO:22, 23, or 24.

8. The method of claim 1 wherein said first protein consists of huntingtin as shown in SEQ ID NO:21.

9. The method of claim 1 wherein the second protein comprises human huntingtin associated protein-1 (HAP1) as shown in SEQ ID NO:24.

10. The method of claim 1 wherein the quantity of said first protein bound to said second protein is determined.

11. The method of claim 1 wherein the quantity of said second protein bound to said first protein is determined.

12. The method of claim 1 wherein the quantity of the first protein which is not bound to said second protein is determined.

13. The method of claim 1 wherein the quantity of said second protein which is not bound to said first protein is determined.

14. A method for identifying compounds which interfere with the binding of a huntingtin associated protein-1 (HAP1) to huntingtin, said compounds being candidate therapeutic agents, said method comprising the steps of:

contacting: a first polypeptide; a second polypeptide; and a compound to be tested for its capacity to interfere with binding of said first and said second polypeptides to each other; wherein the first polypeptide comprises amino acids 1–230 of human huntingtin as shown in SEQ ID NO:21, and the second polypeptide comprises amino acids 378–409 of huntingtin associated protein-1 as shown in SEQ ID NO:22 or 23, or amino acids 105–136 of huntingtin associated protein-1 as shown in SEQ ID NO:24; and determining a quantity of the first polypeptide or the second polypeptide, wherein a compound which diminishes the quantity of the first polvpeptide bound to the second polypeptide when compared to control values is identified as a candidate therapeutic agent.

15. The method of claim 14 wherein an antibody is used to determine the quantity of the first polypeptide or the second polypeptide.

16. The method of claim 15 wherein an antibody specifically immunoreactive with said first polypeptide or said second polypeptide is used to immunoprecipitate bound complexes of said first polypeptide and said second polypeptide.

17. The method of claim 14 wherein one of said first polypeptide and said second polypeptide is fixed to a solid support.

18. The method of claim 14 wherein one of said first polypeptide and said second polvpeptide is labeled.

19. The method of claim 14 wherein said second polypeptide comprises amino acids 105–136 of human huntingtin associated protein-1 (HAP1) as shown in SEQ ID NO:24.

20. The method of claim 14 wherein said second polypeptide comprises amino acids 4–136 of human huntingtin associated protein-1 (HAP1) as shown in SEQ ID NO:24.

21. The method of claim 14 wherein said second polypeptide comprises amino acids 50–136 of human huntingtin associated protein-1 (HAP1) as shown in SEQ ID NO:24.

22. The method of claim 14 wherein said second polypeptide comprises amino acids 75–136 of human huntingtin associated protein-1 (HAP1) as shown in SEQ ID NO:24.

23. The method of claim 14 wherein said first polypeptide which comprises amino acids 1–230 of huntingtin as shown in SEQ ID NO:21 comprises less than all of the complete sequence of amino acids of huntingtin.

24. The method of claim 14 wherein the second polypeptide consists of human huntingtin associated protein-1 (HAP1) as shown in SEQ ID NO:24.

25. The method of claim 14 wherein the first polypeptide consists of human huntingtin as shown in SEQ ID NO:21.

26. The method of claim 14 wherein at least one of said first and said second polypeptides is a fusion polypeptide.

27. The method of claim 26 wherein said fusion polypeptide comprises amino acids 105–136 of human huntingtin associated protein-1 (HAP1) as shown in SEQ ID NO:24.

28. The method of claim 26 wherein said fusion polypeptide comprises amino acids 4–136 of human huntingtin associated protein-1 (HAP1) as shown in SEQ ID NO:24.

29. The method of claim 26 wherein said fusion polypeptide comprises amino acids 50–136 of human huntingtin associated protein-1 (HAP1) as shown in SEQ ID NO:24.

30. The method of claim 26 wherein said fusion polypeptide comprises amino acids 75–136 of human huntingtin associated protein-1 (HAP1) as shown in SEQ ID NO:24.

31. The method of claim 26 wherein said fusion polypeptide comprises amino acids 1–230 of human huntingtin as shown in SEQ ID NO:21.

32. The method of claim 14 wherein the quantity of said first polypeptide bound to said second polypeptide is determined.

33. The method of claim 14 wherein the quantity of said second polypeptide bound to said first polypeptide is determined.

34. The method of claim 14 wherein the quantity of said first polypeptide which is not bound to said second polypeptide is determined.

35. The method of claim 14 wherein the quantity of said second polypeptide which is not bound to said first polypeptide is determined.

36. A method of determining the quantity of human huntingtin which binds to huntingtin associated protein-1 (HAP1), or of huntingtin associated protein-1 (HAP1) which binds to human huntingtin, said method comprising:

contacting: a first protein and a second protein, wherein the second protein consists of huntingtin associated protein-1 (HAP1), as shown in SEQ ID NO:22, 23, or 24 and the first protein consists of human huntingtin as shown in SEQ ID NO:21; and determining a quantity of the first protein or a quantity of the second protein which is bound to the other protein.

37. The method of claim 36 wherein the quantity of said first protein bound to said second protein is determined.

38. The method of claim 36 wherein the quantity of said second protein bound to said first protein is determined.

39. The method of claim 36 wherein the quantity of the first protein bound to the second protein is determined by measuring the first protein which is not bound to said second protein.

40. The method of claim 36 wherein the quantity of the second protein bound to the first protein is determined by measuring the second protein which is not bound to said first protein.

* * * * *

UNITED STATES PATENT AND TRADEMARK OFFICE

CERTIFICATE OF CORRECTION

PATENT NO. : 6,093,549

DATED : July 25, 2000

INVENTOR(S) : Christopher A. ROSS, *et al.*

It is certified that error appears in the above-indentified patent and that said Letters Patent is hereby corrected as shown below:

In claim 14, column 59, line 17:

The word "polvpeptide" has been replaced with --polypeptide--.

In claim 18, column 59, line 32:

The word "polvpeptide" has been replaced with --polypeptide--.

Signed and Sealed this

Tenth Day of April, 2001

Attest:

Nicholas P. Godici

NICHOLAS P. GODICI

*Attesting Officer*

*Acting Director of the United States Patent and Trademark Office*

SEQUENCE LISTING

```
<160> NUMBER OF SEQ ID NOS: 25

<210> SEQ ID NO 1
<211> LENGTH: 21
<212> TYPE: DNA
<213> ORGANISM: Rattus norvegicus

<400> SEQUENCE: 1

gatgatctcc ttcagctcta c                                              21


<210> SEQ ID NO 2
<211> LENGTH: 24
<212> TYPE: DNA
<213> ORGANISM: Rattus norvegicus

<400> SEQUENCE: 2

ccagttggac agttgctgga ggac                                           24


<210> SEQ ID NO 3
<211> LENGTH: 21
<212> TYPE: DNA
<213> ORGANISM: Rattus norvegicus

<400> SEQUENCE: 3

accactgccc acagctggaa g                                              21


<210> SEQ ID NO 4
<211> LENGTH: 20
<212> TYPE: DNA
<213> ORGANISM: Rattus norvegicus

<400> SEQUENCE: 4

catagtgggt gacagaacct                                                20


<210> SEQ ID NO 5
<211> LENGTH: 22
<212> TYPE: DNA
<213> ORGANISM: Rattus norvegicus

<400> SEQUENCE: 5

agcagaagct gaagctgctg ga                                             22


<210> SEQ ID NO 6
<211> LENGTH: 20
<212> TYPE: DNA
<213> ORGANISM: Rattus norvegicus

<400> SEQUENCE: 6

agaacctgca ggcattgagg                                                20


<210> SEQ ID NO 7
<211> LENGTH: 21
<212> TYPE: DNA
<213> ORGANISM: Homo sapiens
```

-continued

<400> SEQUENCE: 7
atgctcattc tggagtgtgt g 21

<210> SEQ ID NO 8
<211> LENGTH: 20
<212> TYPE: DNA
<213> ORGANISM: Homo sapiens

<400> SEQUENCE: 8
agaacctgca ggcattgagg 20

<210> SEQ ID NO 9
<211> LENGTH: 960
<212> TYPE: DNA
<213> ORGANISM: Homo sapiens

<400> SEQUENCE: 9
ctctactcag attctgatga ggaggatgag gatgaagaag aggaggagga agaaaaggag 60
gcagaagagg aacaggaaga agaagaagca gaggaagacc tgcagtgtgc tcatccctgt 120
gatgccccta agctgatttc gcaggaggca ttgctgcacc agcaccactg cccacagctg 180
gaagccttgc aggagaagct gaggctgctg gaggaggaga atcatcagct gagagaagag 240
gcctctcaac tcgacactct tgaggatgag gaacagatgc tcattctgga gtgtgtggag 300
cagttttcgg aggccagcca acagatggct gagctgtcgg aggtgctggt gctcaggctg 360
gaaaactatg aacggcagca gcaggaggtc gctcggctgc aggcccaggt gctgaagctg 420
cagcagcgct gccggatgta tggggctgag actgaaaagt tgcagaagca gctggcttcg 480
gagaaggaaa tccagatgca gctccaggaa gaggagactc tgcctggttt ccaggagacg 540
ctggctgagg agctcagaac gtctctaagg aggatgatct cagaccctgt gtattttatg 600
gagaggaatt atgagatgcc cagaggggac acatccagcc taaggtatga ttttcgctac 660
agtgaggatc gagagcaggt gcgggggttt gaggctgagg aagggttgat gctggcagcg 720
gatatcatgc ggggggaaga tttcacgcct gcggaggagt tggtgcccca ggaggagctg 780
ggggctgcca agaaggtgcc ggctgaggaa ggggtgatgg aagaggcaga gctggtgtca 840
gaggagaccg agggctggga ggaggtggaa ctggagctgg atgaggcaac gcggatgaac 900
gtggtgacat caaccctgga ggccagcggc ttgggccctt cacacctgga catgaattat 960

<210> SEQ ID NO 10
<211> LENGTH: 3708
<212> TYPE: DNA
<213> ORGANISM: Rattus norvegicus

<400> SEQUENCE: 10
ggaattcggc acgaggcgac agcggactgc agagtcaaga tgcgcccgaa ggaccaggtg 60
cagagcagtg ccggggacgg gacggggtcg ggggacccag caacaggcac ccccacgacc 120
cagcctgcag cggatcccgc tccggagccc tcggcagagc ccaaacctgc tccggcgcag 180
ggaaccgggt ccggacagaa atcaggatcc cgaaccaaga caggaggaag cttttgtagg 240
tccaggatcc gtggcgactc ggacgcacca tggacccgct acatattcca ggggccttac 300
ggtccccggg ctactggcct gggcactgga agggctgagg gaatctggaa gacgccagcc 360
gcgtacatcg gccgaaggcc cggcgtgtcc ggccctgagc gcgcggcgtt tattcgagag 420
ctgcaggaag cgctgtgtcc taatccactg cccaggaaga agatcaccga agatgatatc 480
aaagtgatgt tgtatttgct ggaagagaaa gaacgggacc tgaacacagc cgctcgcatc 540

-continued

```
ggccagtccc tggtgaaaca gaatagtgtt ctgatggagg agaataacaa gctggaaacc    600
atgctgggct cagccagaga ggagatttta catctccgga agcaggtgaa cctgcgagat    660
gatctccttc agctctactc ggactccgat gacgatgagg aggatgaaga ggatgaggaa    720
gaggaagagg gagaagagga ggaacgagaa ggacagaggg accaagatca gcagcacgac    780
catccctatg gtgcccccaa gccgccccct aaggctgaga cgctgcacca ctgcccacag    840
ctggaagccc tgaagcagaa gctgaaactg ctggaagaag agaacgacca tcttcgagag    900
gaggcctccc accttgacaa cctggaagac aaagaacaga tgctcattct ggagtgtgtg    960
gaacagtttt ctgaagccag ccagcagatg gcagagctat ccgaggtgtt ggtgctgagg   1020
ctggaaggct atgagaggca gcagaaggag atcactcagc tgcaggccga gatcaccaag   1080
ctacaacagc gttgtcagtc ttatggggcc cagacggaga aactgcagca gcagctggcc   1140
tcagagaagg gagtccaccc agagagcctg cgagctggct cccacatgca ggattatgga   1200
agcaggcctc gtgaacgcca ggaggatggg aagagccatc gtcagcgttc ctcaatgcct   1260
gcaggttctg tcacccacta tggatacagt gtgcctctgg atgcacttcc aagtttccca   1320
gagacactgg cggaggagct ccggacatcc ctgaggaagt tcatcactga ccctgcgtat   1380
ttcatggaga gatgtgacac tcgctgcaga gaggaacgaa agaaggagca ggggacaatg   1440
ccacccccac cggtgcaaga tctcaagccg cctgaagatt tcgaggctcc agaggagctg   1500
gttcctgagg aggagctggg ggccatagaa gaggtgggga cagctgagga tgggccggca   1560
gaagagacag agcaggcatc tgaggagacc gaggcctggg aggaggtgga accggaggtg   1620
gacgaggcca caaggatgaa tgtggtggtc tctgccctgg aggccagcgg cctgggccct   1680
tcacacctgg acatgaagta tgtcctccag caactgtcca actggcagga cgcccattct   1740
aagcggcagc agaagcagaa ggtggtcccg aaaggtgagt gttcccgcag aggacaccct   1800
cctgccagtg ggacaagcta ccgatcatca accctatgag aggtgagagt aggtgagacc   1860
ccccaccccc aagggctcac ttacctcacc ttggtcccac tcggtgtgct gatttgcatg   1920
gactttgcat actatttgca tagtatttac atacttgcct ccagtccccc ttggctagaa   1980
ctgctgcctc agtgtttatt tatgcaaaat ttgcttacaa gtccagctat ccatccacct   2040
tcttcctggg ggggctgaac tgggaatcag ggttggacta tacactcctt tgtacctcaa   2100
cttcctgtct ctgcccatcc tctccctatc cccaattcct ctaccctcaa gactccccag   2160
ccccgcagca gcaaacaaac atgggggggcg ggatcgtgga gcagcagccc atagtgccga   2220
cccaggactc tcagaggctg gaggaggaca gggccactca ctctcccagt gccagggagg   2280
aagaggggcc ttctggggcc acctaggcct ggaacgaagg cctctgccag caaaggccac   2340
agttggacca atcccccggg tgagtgtggg gctcccgcag ggtggtaggg gcgggtcagg   2400
gtctcctctg cctatctgga aaccccagtt cctaggagat gctgtccgtg aaatcagatg   2460
atttagcatt ggatctcttt ctgtgttagc tcctttcgtc ttctggccct gtgggtgggt   2520
ggatgtgatt gtgcaccatt tattagaaga ggaatctgaa gttcagagat ctgagatgac   2580
ttggccaagg tcatacagct aggagcagat ctgagccggt gtctcttgag gactgaaacc   2640
ctggcctggt ctcactgccg tccacacctc ctcctgctcc cgtccttgag ctccacctga   2700
agctttggca gcctccctca tgtcggtctg ttgccatttt tggggggcac cagtgagtgg   2760
aacatcactg gctgcagcac agtcaaatca tgcaggttgt aagctgagtc agcacacccg   2820
tggctgacca cgggagaccg ggagacctga gtaacggcta gcggtggctt tctgttgtct   2880
```

-continued

```
cctgacccgg ctgactgggt ttgagggtga tctgtctccc ggttcacccc cttctcttcc   2940

tggctttgct gtttctcagc agcctgaaga agaccctcag acagctcgag acccctcctt   3000

ccactgcctg gccaagtccg acccttcctt gctttcctct gagacaggac ccccaccccc   3060

atgtctgtca gcagttctcc ctctgtcttg atagatcttt cccctcttgt aggacaggct   3120

gaaagaaccc cagtccctca ttctgaaact ggggccaaag ctgtgcctgc tggagcccca   3180

gggggtggaa gcaacctgtg ggtagattgg ttggttacca gacccagctc tgagatggtg   3240

tgggtgcgca catccctagg gtaggcagtt attgggggga ccctttctat cccttgaacc   3300

tctcacgtaa agggacttcc ccagtcctgg ttggcttttg gaacctggtc cttcttgctg   3360

ttttttaccc ttccccgttt ctattactgc gtgtaacgta aagtgtatct gagtgagggt   3420

ggtgggaacc ctctgtccag tgctgtctct gtctcctatg gcctgtgagt ttccttctag   3480

agttctactc ttctccacct ctttgctcat acagagctgt ggccttggcg cctgccctgc   3540

ttctgcagtg cttcattgtc tcgtagcttg tcagctgaca ccggaaccgc ggacgggacg   3600

aagacgtcac gaagtaacag agcatcgaac agtcgatttg tattgatgta tgtgccaatg   3660

tgggaaataa agaccttgtg agataaaaaa aaaaaaaaaa aaaaaaaa                3708
```

<210> SEQ ID NO 11
<211> LENGTH: 3201
<212> TYPE: DNA
<213> ORGANISM: Rattus norvegicus

<400> SEQUENCE: 11

```
ggaattcggc acgaggcgac agcggactgc agagtcaaga tgcgcccgaa ggaccaggtg     60

cagagcagtg ccggggacgg gacggggtcg ggggacccag caacaggcac ccccacgacc    120

cagcctgcag cggatcccgc tccggagccc tcggcagagc ccaaacctgc tccggcgcag    180

ggaaccgggt ccggacagaa atcaggatcc cgaaccaaga caggaggaag cttttgtagg    240

tccaggatcc gtggcgactc ggacgcacca tggacccgct acatattcca ggggccttac    300

ggtccccggg ctactggcct gggcactgga agggctgagg gaatctggaa gacgccagcc    360

gcgtacatcg gccgaaggcc cggcgtgtcc ggccctgagc gcgcggcgtt tattcgagag    420

ctgcaggaag cgctgtgtcc taatccactg cccaggaaga agatcaccga agatgatatc    480

aaagtgatgt tgtatttgct ggaagagaaa gaacgggacc tgaacacagc cgctcgcatc    540

ggccagtccc tggtgaaaca gaatagtgtt ctgatggagg agaataacaa gctggaaacc    600

atgctgggct cagccagaga ggagatttta catctccgga agcaggtgaa cctgcgagat    660

gatctccttc agctctactc ggactccgat gacgatgagg aggatgaaga ggatgaggaa    720

gaggaagagg gagaagagga ggaacgagaa ggacagaggg accaagatca gcagcacgac    780

catccctatg gtgcccccaa gccgccccct aaggctgaga cgctgcacca ctgcccacag    840

ctggaagccc tgaagcagaa gctgaaactg ctggaagaag agaacgacca tcttcgagag    900

gaggcctccc accttgacaa cctggaagac aaagaacaga tgctcattct ggagtgtgtg    960

gaacagtttt ctgaagccag ccagcagatg gcagagctat ccgaggtgtt ggtgctgagg   1020

ctggaaggct atgagaggca gcagaaggag atcactcagc tgcaggccga gatcaccaag   1080

ctacaacagc gttgtcagtc ttatggggcc cagacggaga aactgcagca gcagctggcc   1140

tcagagaagg gagtccaccc agagagcctg cgagctggct cccacatgca ggattatgga   1200

agcaggcctc gtgaacgcca ggaggatggg aagagccatc gtcagcgttc ctcaatgcct   1260

gcaggttctg tcacccacta tggatacagt gtgcctctgg atgcacttcc aagtttccca   1320
```

-continued gagacactgg cggaggagct ccggacatcc ctgaggaagt tcatcactga ccctgcgtat 1380
ttcatggaga gatgtgacac tcgctgcaga gaggaacgaa agaaggagca ggggacaatg 1440 ccaccccac cggtgcaaga tctcaagccg cctgaagatt tcgaggctcc agaggagctg 1500
gttcctgagg aggagctggg ggccatagaa gaggtgggga cagctgagga tgggccggca 1560
gaagagacag agcaggcatc tgaggagacc gaggcctggg aggaggtgga accggaggtg 1620
gacgaggcca caaggatgaa tgtggtggtc tctgccctgg aggccagcgg cctgggccct 1680
tcacacctgg acatgaagta tgtcctccag caactgtcca actggcagga cgcccattct 1740
aagcggcagc agaagcagaa ggtggtcccg aaagactccc cagccccgca gcagcaaaca 1800
aacatggggg gcgggatcgt ggagcagcag cccatagtgc cgacccagga ctctcagagg 1860
ctggaggagg acagggccac tcactctccc agtgccaggg aggaagaggg gccttctggg 1920
gccacctagg cctggaacga aggcctctgc cagcaaaggc cacagttgga ccaatccccc 1980
ggctcctttc gtcttctggc cctgtgggtg ggtggatgtg attgtgcacc atttattaga 2040
agaggaatct gaagttcaga gatctgagat gacttggcca aggtcataca gctaggagca 2100
gatctgagcc ggtgtctctt gaggactgaa accctggcct ggtctcactg ccgtccacac 2160
ctcctcctgc tcccgtcctt gagctccacc tgaagctttg gcagcctccc tcatgtcggt 2220
ctgttgccat ttttgggggg caccagtgag tggaacatca ctggctgcag cacagtcaaa 2280
tcatgcaggt tgtaagctga gtcagcacac ccgtggctga ccacgggaga ccgggagacc 2340
tgagtaacgg ctagcggtgg ctttctgttg tctcctgacc cggctgactg ggtttgaggg 2400
tgatctgtct cccggttcac cccttctct tcctggcttt gctgtttctc agcagcctga 2460
agaagaccct cagacagctc gagacccctc cttccactgc ctggccaagt ccgacccttc 2520
cttgctttcc tctgagacag gaccccacc cccatgtctg tcagcagttc tccctctgtc 2580
ttgatagatc tttcccctct tgtaggacag gctgaaagaa ccccagtccc tcattctgaa 2640
actggggcca aagctgtgcc tgctggagcc ccaggggggtg gaagcaacct gtgggtagat 2700
tggttggtta ccagacccag ctctgagatg gtgtgggtgc gcacatccct agggtaggca 2760
gttattgggg ggaccctttc tatcccttga acctctcacg taaagggact tccccagtcc 2820
tggttggctt ttggaacctg gtccttcttg ctgtttttta cccttccccg tttctattac 2880
tgcgtgtaac gtaaagtgta tctgagtgag ggtggtggga accctctgtc cagtgctgtc 2940
tctgtctcct atggcctgtg agtttccttc tagagttcta ctcttctcca cctctttgct 3000
catacagagc tgtggccttg gcgcctgccc tgcttctgca gtgcttcatt gtctcgtagc 3060
ttgtcagctg acaccggaac cgcggacggg acgaagacgt cacgaagtaa cagagcatcg 3120
aacagtcgat ttgtattgat gtatgtgcca atgtgggaaa taaagacctt gtgagataaa 3180
aaaaaaaaaa aaaaaaaaaa a 3201

<210> SEQ ID NO 12
<211> LENGTH: 378
<212> TYPE: DNA
<213> ORGANISM: Homo sapiens

<400> SEQUENCE: 12
gaggaggaga atcatcagct gagagaagag gcctctcaac tcgacactct tgaggatgag 60
gaacagatgc tcattctgga gtgtgtggag cagttttctg aagccagcca gcagatggca 120
gagctatccg aggtgttggt gctgaggctg gaaggctatg agaggcagca gaaggagatc 180

-continued

```
actcagctgc aggccgagat caccaagcta caacagcgtt gtcagtctta tggggcccag    240

acggagaaac tgcagcagca gctggcctca gagaagggag tccacccaga gagcctgcga    300

gctggctccc acatgcagga ttatggaagc aggcctcgtg aacgccagga ggatgggaag    360

agccatcgtc agcgttcc                                                  378
```

```
<210> SEQ ID NO 13
<211> LENGTH: 10348
<212> TYPE: DNA
<213> ORGANISM: Homo sapiens

<400> SEQUENCE: 13

ttgctgtgtg aggcagaacc tgcgggggca ggggcgggct ggttccctgg ccagccattg     60

gcagagtccg caggctaggg ctgtcaatca tgctggccgg cgtggccccg cctccgccgg    120

cgcggccccg cctccgccgg cgcacgtctg ggacgcaagg cgccgtgggg gctgccggga    180

cgggtccaag atggacggcc gctcaggttc tgcttttacc tgcggcccag agccccattc    240

attgccccgg tgctgagcgg cgccgcgagt cggcccgagg cctccgggga ctgccgtgcc    300

gggcgggaga ccgccatggc gaccctggaa aagctgatga aggccttcga gtccctcaag    360

tccttccagc agcagcagca gcagcagcag cagcagcagc agcagcagca gcagcagcag    420

cagcagcagc aacagccgcc accgccgccg ccgccgccgc cgcctcctca gcttcctcag    480

ccgccgccgc aggcacagcc gctgctgcct cagccgcagc cgcccccgcc gccgccccccg    540

ccgccacccg gcccggctgt ggctgaggag ccgctgcacc gaccaaagaa agaactttca    600

gctaccaaga aagaccgtgt gaatcattgt ctgacaatat gtgaaaacat agtggcacag    660

tctgtcagaa attctccaga atttcagaaa cttctgggca tcgctatgga actttttctg    720

ctgtgcagtg atgacgcaga gtcagatgtc aggatggtgg ctgacgaatg cctcaacaaa    780

gttatcaaag ctttgatgga ttctaatctt ccaaggttac agctcgagct ctataaggaa    840

attaaaaaga atggtgcccc tcggagtttg cgtgctgccc tgtggaggtt tgctgagctg    900

gctcacctgg ttcggcctca gaaatgcagg ccttacctgg tgaaccttct gccgtgcctg    960

actcgaacaa gcaagagacc cgaagaatca gtccaggaga ccttggctgc agctgttccc   1020

aaaattatgg cttcttttgg caattttgca aatgacaatg aaattaaggt tttgttaaag   1080

gccttcatag cgaacctgaa gtcaagctcc cccaccattc ggcggacagc ggctggatca   1140

gcagtgagca tctgccagca ctcaagaagg acacaatatt tctatagttg gctactaaat   1200

gtgctcttag gcttactcgt tcctgtcgag gatgaacact ccactctgct gattcttggc   1260

gtgctgctca ccctgaggta tttggtgccc ttgctgcagc agcaggtcaa ggacacaagc   1320

ctgaaaggca gcttcggagt gacaaggaaa gaaatggaag tctctccttc tgcagagcag   1380

cttgtccagg tttatgaact gacgttacat catacacagc accaagacca caatgttgtg   1440

accggagccc tggagctgtt gcagcagctc ttcagaacgc ctccacccga gcttctgcaa   1500

accctgaccg cagtcggggg cattgggcag ctcaccgctg ctaaggagga gtctggtggc   1560

cgaagccgta gtgggagtat tgtggaactt atagctggag ggggttcctc atgcagccct   1620

gtcctttcaa gaaaacaaaa aggcaaagtg ctcttaggag aagaagaagc cttggaggat   1680

gactctgaat cgagatcgga tgtcagcagc tctgccttaa cagcctcagt gaaggatgag   1740

atcagtggag agctggctgc ttcttcaggg gtttccactc cagggtcagc aggtcatgac   1800

atcatcacag aacagccacg gtcacagcac acactgcagg cggactcagt ggatctggcc   1860

agctgtgact tgacaagctc tgccactgat ggggatgagg aggatatctt gagccacagc   1920
```

-continued

```
tccagccagg tcagcgccgt cccatctgac cctgccatgg acctgaatga tgggacccag   1980
gcctcgtcgc ccatcagcga cagctcccag accaccaccg aagggcctga ttcagctgtt   2040
accccttcag acagttctga aattgtgtta gacggtaccg acaaccagta tttgggcctg   2100
cagattggac agccccagga tgaagatgag gaagccacag gtattcttcc tgatgaagcc   2160
tcggaggcct tcaggaactc ttccatggcc cttcaacagg cacatttatt gaaaaacatg   2220
agtcactgca ggcagccttc tgacagcagt gttgataaat ttgtgttgag agatgaagct   2280
actgaaccgg gtgatcaaga aaacaagcct tgccgcatca aaggtgacat tggacagtcc   2340
actgatgatg actctgcacc tcttgtccat tgtgtccgcc ttttatctgc ttcgtttttg   2400
ctaacagggg gaaaaaatgt gctggttccg gacagggatg tgagggtcag cgtgaaggcc   2460
ctggccctca gctgtgtggg agcagctgtg gccctccacc cggaatcttt cttcagcaaa   2520
ctctataaag ttcctcttga caccacggaa taccctgagg aacagtatgt ctcagacatc   2580
ttgaactaca tcgatcatgg agacccacag gttcgaggag ccactgccat tctctgtggg   2640
accctcatct gctccatcct cagcaggtcc cgcttccacg tgggagattg gatgggcacc   2700
attagaaccc tcacaggaaa tacattttct ttggcggatt gcattccttt gctgcggaaa   2760
acactgaagg atgagtcttc tgttacttgc aagttagctt gtacagctgt gaggaactgt   2820
gtcatgagtc tctgcagcag cagctacagt gagttaggac tgcagctgat catcgatgtg   2880
ctgactctga ggaacagttc ctattggctg gtgaggacag agcttctgga aacccttgca   2940
gagattgact tcaggctggt gagctttttg gaggcaaaag cagaaaactt acacagaggg   3000
gctcatcatt atacagggct tttaaaactg caagaacgag tgctcaataa tgttgtcatc   3060
catttgcttg gagatgaaga ccccagggtg cgacatgttg ccgcagcatc actaattagg   3120
cttgtcccaa agctgtttta taaatgtgac caaggacaag ctgatccagt agtggccgtg   3180
gcaagagatc aaagcagtgt ttacctgaaa cttctcatgc atgagacgca gcctccatct   3240
catttctccg tcagcacaat aaccagaata tatagaggct ataacctact accaagcata   3300
acagacgtca ctatggaaaa taacctttca agagttattg cagcagtttc tcatgaacta   3360
atcacatcaa ccaccagagc actcacattt ggatgctgtg aagctttgtg tcttctttcc   3420
actgccttcc cagtttgcat ttggagttta ggttggcact gtggagtgcc tccactgagt   3480
gcctcagatg agtctaggaa gagctgtacc gttgggatgg ccacaatgat tctgaccctg   3540
ctctcgtcag cttggttccc attggatctc tcagcccatc aagatgcttt gattttggcc   3600
ggaaacttgc ttgcagccag tgctcccaaa tctctgagaa gttcatgggc ctctgaagaa   3660
gaagccaacc cagcagccac caagcaagag gaggtctggc cagccctggg ggaccgggcc   3720
ctggtgccca tggtggagca gctcttctct cacctgctga aggtgattaa catttgtgcc   3780
cacgtcctgg atgacgtggc tcctggaccc gcaataaagg cagccttgcc ttctctaaca   3840
aaccccccctt ctctaagtcc catccgacga aaggggaagg agaaagaacc aggagaacaa   3900
gcatctgtac cgttgagtcc caagaaaggc agtgaggcca gtgcagcttc tagacaatct   3960
gatacctcag gtcctgttac aacaagtaaa tcctcatcac tggggagttt ctatcatctt   4020
ccttcatacc tcaaactgca tgatgtcctg aaagctacac acgctaacta caaggtcacg   4080
ctggatcttc agaacagcac ggaaaagttt ggagggtttc tccgctcagc cttggatgtt   4140
ctttctcaga tactagagct ggccacactg caggacattg ggaagtgtgt tgaagagatc   4200
ctaggatacc tgaaatcctg ctttagtcga gaaccaatga tggcaactgt ttgtgttcaa   4260
```

-continued caattgttga agactctctt tggcacaaac ttggcctccc agtttgatgg cttatcttcc 4320
aaccccagca agtcacaagg ccgagcacag cgccttggct cctccagtgt gaggccaggc 4380
ttgtaccact actgcttcat ggccccgtac acccacttca cccaggccct cgctgacgcc 4440
agcctgagga acatggtgca ggcggagcag gagaacgaca cctcgggatg gtttgatgtc 4500
ctccagaaag tgtctaccca gttgaagaca aacctcacga gtgtcacaaa gaaccgtgca 4560
gataagaatg ctattcataa tcacattcgt ttgtttgaac ctcttgttat aaaagcttta 4620
aaacagtaca cgactacaac atgtgtgcag ttacagaagc aggttttaga tttgctggcg 4680
cagctggttc agttacgggt taattactgt cttctggatt cagatcaggt gtttattggc 4740
tttgtattga aacagtttga atacattgaa gtgggccagt tcagggaatc agaggcaatc 4800
attccaaaca tctttttctt cttggtatta ctatcttatg aacgctatca ttcaaaacag 4860
atcattggaa ttcctaaaat cattcagctc tgtgatggca tcatggccag tggaaggaag 4920
gctgtgacac atgccatacc ggctctgcag cccatagtcc acgacctctt tgtattaaga 4980
ggaacaaata aagctgatgc aggaaaagag cttgaaaccc aaaaagaggt ggtggtgtca 5040
atgttactga gactcatcca gtaccatcag gtgttggaga tgttcattct tgtcctgcag 5100
cagtgccaca aggagaatga agacaagtgg aagcgactgt ctcgacagat agctgacatc 5160
atcctcccaa tgttagccaa acagcagatg cacattgact ctcatgaagc ccttggagtg 5220
ttaaatacat tatttgagat tttggcccct tcctccctcc gtccggtaga catgctttta 5280
cggagtatgt tcgtcactcc aaacacaatg gcgtccgtga gcactgttca actgtggata 5340
tcgggaattc tggccatttt gagggttctg atttcccagt caactgaaga tattgttctt 5400
tctcgtattc aggagctctc cttctctccg tatttaatct cctgtacagt aattaatagg 5460
ttaagagatg gggacagtac ttcaacgcta gaagaacaca gtgaagggaa acaaataaag 5520
aatttgccag aagaaacatt ttcaaggttt ctattacaac tggttggtat tcttttagaa 5580
gacattgtta caaaacagct gaaggtggaa atgagtgagc agcaacatac tttctattgc 5640
caggaactag gcacactgct aatgtgtctg atccacatct tcaagtctgg aatgttccgg 5700
agaatcacag cagctgccac taggctgttc cgcagtgatg gctgtggcgg cagtttctac 5760
accctggaca gcttgaactt gcgggctcgt tccatgatca ccacccaccc ggccctggtg 5820
ctgctctggt gtcagatact gctgcttgtc aaccacaccg actaccgctg gtgggcagaa 5880
gtgcagcaga ccccgaaaag acacagtctg tccagcacaa agttacttag tccccagatg 5940
tctggagaag aggaggattc tgacttggca gccaaacttg gaatgtgcaa tagagaaata 6000
gtacgaagag ggctctcat tctcttctgt gattatgtct gtcagaacct ccatgactcc 6060
gagcacttaa cgtggctcat tgtaaatcac attcaagatc tgatcagcct ttcccacgag 6120
cctccagtac aggacttcat cagtgccgtt catcggaact ctgctgccag cggcctgttc 6180
atccaggcaa ttcagtctcg ttgtgaaaac ctttcaactc caaccatgct gaagaaaact 6240
cttcagtgct tggaggggat ccatctcagc cagtcgggag ctgtgctcac gctgtatgtg 6300
gacaggcttc tgtgcacccc tttccgtgtg ctggctcgca tggtcgacat ccttgcttgt 6360
cgccgggtag aaatgcttct ggctgcaaat ttacagagca gcatggccca gttgccaatg 6420
gaagaactca acagaatcca ggaatacctt cagagcagcg ggctcgctca gagacaccaa 6480
aggctctatt ccctgctgga caggtttcgt ctctccacca tgcaagactc acttagtccc 6540
tctcctccag tctcttccca cccgctggac ggggatgggc acgtgtcact ggaaacagtg 6600
agtccggaca aagactggta cgttcatctt gtcaaatccc agtgttggac caggtcagat 6660

-continued tctgcactgc tggaaggtgc agagctggtg aatcggattc ctgctgaaga tatgaatgcc 6720
ttcatgatga actcggagtt caacctaagc ctgctagctc catgcttaag cctagggatg 6780
agtgaaattt ctggtggcca gaagagtgcc ctttttgaag cagcccgtga ggtgactctg 6840
gcccgtgtga gcggcaccgt gcagcagctc cctgctgtcc atcatgtctt ccagcccgag 6900
ctgcctgcag agccggcggc ctactggagc aagttgaatg atctgtttgg ggatgctgca 6960
ctgtatcagt ccctgcccac tctggcccgg gccctggcac agtacctggt ggtggtctcc 7020
aaactgccca gtcatttgca ccttcctcct gagaaagaga aggacattgt gaaattcgtg 7080
gtggcaaccc ttgaggccct gtcctggcat ttgatccatg agcagatccc gctgagtctg 7140
gatctccagg cagggctgga ctgctgctgc ctggccctgc agctgcctgg cctctggagc 7200
gtggtctcct ccacagagtt tgtgacccac gcctgctccc tcatctactg tgtgcacttc 7260
atcctggagg ccgttgcagt gcagcctgga gagcagcttc ttagtccaga aagaaggaca 7320
aataccccaa aagccatcag cgaggaggag gaggaagtag atccaaacac acagaatcct 7380
aagtatatca ctgcagcctg tgagatggtg gcagaaatgg tggagtctct gcagtcggtg 7440
ttggccttgg gtcataaaag gaatagcggc gtgccggcgt ttctcacgcc attgctcagg 7500
aacatcatca tcagcctggc ccgcctgccc cttgtcaaca gctacacacg tgtgcccccca 7560
ctggtgtgga agcttggatg gtcacccaaa ccgggagggg attttggcac agcattccct 7620
gagatccccg tggagttcct ccaggaaaag gaagtcttta aggagttcat ctaccgcatc 7680
aacacactag gctggaccag tcgtactcag tttgaagaaa cttgggccac cctccttggt 7740
gtcctggtga cgcagcccct cgtgatggag caggaggaga gcccaccaga agaagacaca 7800
gagaggaccc agatcaacgt cctggccgtg caggccatca cctcactggt gctcagtgca 7860
atgactgtgc ctgtggccgg caacccagct gtaagctgct tggagcagca gccccggaac 7920
aagcctctga aagctctcga caccaggttt gggaggaagc tgagcattat cagagggatt 7980
gtggagcaag agattcaagc aatggtttca aagagagaga atattgccac ccatcattta 8040
tatcaggcat gggatcctgt cccttctctg tctccggcta ctacaggtgc cctcatcagc 8100
cacgagaagc tgctgctaca gatcaacccc gagcgggagc tggggagcat gagctacaaa 8160
ctcggccagg tgtccataca ctccgtgtgg ctggggaaca gcatcacacc cctgagggag 8220
gaggaatggg acgaggaaga ggaggaggag gccgacgccc ctgcaccttc gtcaccaccc 8280
acgtctccag tcaactccag gaaacaccgg gctggagttg acatccactc ctgttcgcag 8340
tttttgcttg agttgtacag ccgctggatc ctgccgtcca gctcagccag gaggaccccg 8400
gccatcctga tcagtgaggt ggtcagatcc cttctagtgg tctcagactt gttcaccgag 8460
cgcaaccagt ttgagctgat gtatgtgacg ctgacagaac tgcgaagggt gcacccttca 8520
gaagacgaga tcctcgctca gtacctggtg cctgccacct gcaaggcagc tgccgtcctt 8580
gggatggaca aggccgtggc ggagcctgtc agccgcctgc tggagagcac gctcaggagc 8640
agccacctgc ccagcagggt tggagccctg cacggcgtcc tctatgtgct ggagtgcgac 8700
ctgctggacg acactgccaa gcagctcatc ccggtcatca gcgactatct cctctccaac 8760
ctgaaaggga tcgcccactg cgtgaacatt cacagccagc agcacgtact ggtcatgtgt 8820
gccactgcgt tttacctcat tgagaactat cctctggacg tagggccgga attttcagca 8880
tcaataatac agatgtgtgg ggtgatgctg tctggaagtg aggagtccac cccctccatc 8940
atttaccact gtgccctcag aggcctggag cgcctcctgc tctctgagca gctctcccgc 9000

-continued

```
ctggatgcag aatcgctggt caagctgagt gtggacagag tgaacgtgca cagcccgcac   9060

cgggccatgg cggctctggg cctgatgctc acctgcatgt acacaggaaa ggagaaagtc   9120

agtccgggta gaacttcaga ccctaatcct gcagcccccg acagcgagtc agtgattgtt   9180

gctatggagc gggtatctgt tctttttgat aggatcagga aaggctttcc ttgtgaagcc   9240

agagtggtgg ccaggatcct gccccagttt ctagacgact tcttcccacc ccaggacatc   9300

atgaacaaag tcatcggaga gtttctgtcc aaccagcagc catacccccca gttcatggcc   9360

accgtggtgt ataaggtgtt tcagactctg cacagcaccg ggcagtcgtc catggtccgg   9420

gactgggtca tgctgtccct ctccaacttc acgcagaggg ccccggtcgc catggccacg   9480

tggagcctct cctgcttctt tgtcagcgcg tccaccagcc cgtgggtcgc ggcgatcctc   9540

ccacatgtca tcagcaggat gggcaagctg gagcaggtgg acgtgaacct tttctgcctg   9600

gtcgccacag acttctacag acaccagata gaggaggagc tcgaccgcag ggccttccag   9660

tctgtgcttg aggtggttgc agccccagga agcccatatc accggctgct gacttgttta   9720

cgaaatgtcc acaaggtcac cacctgctga gcgccatggt gggagagact gtgaggcggc   9780

agctggggcc ggagcctttg gaagtctgtg cccttgtgcc ctgcctccac cgagccagct   9840

tggtccctat gggcttccgc acatgccgcg ggcggccagg caacgtgcgt gtctctgcca   9900

tgtggcagaa gtgctctttg tggcagtggc caggcaggga gtgtctgcag tcctggtggg   9960

gctgagcctg aggccttcca gaaagcagga gcagctgtgc tgcaccccat gtgggtgacc  10020

aggtcctttc tcctgatagt cacctgctgg ttgttgccag gttgcagctg ctcttgcatc  10080

tgggccagaa gtcctccctc ctgcaggctg gctgttggcc cctctgctgt cctgcagtag  10140

aaggtgccgt gagcaggctt tgggaacact ggcctgggtc tccctggtgg ggtgtgcatg  10200

ccacgccccg tgtctggatg cacagatgcc atggcctgtg ctgggccagt ggctgggggt  10260

gctagacacc cggcaccatt ctcccttctc tcttttcttc tcaggattta aaatttaatt  10320

atatcagtaa agagattaat tttaacgt                                      10348
```

<210> SEQ ID NO 14
<211> LENGTH: 7
<212> TYPE: PRT
<213> ORGANISM: Rattus norvegicus

<400> SEQUENCE: 14

Asp Asp Leu Leu Gln Leu Tyr
1 5

<210> SEQ ID NO 15
<211> LENGTH: 6
<212> TYPE: PRT
<213> ORGANISM: Rattus norvegicus

<400> SEQUENCE: 15

Val Leu Gln Gln Leu Ser
1 5

<210> SEQ ID NO 16
<211> LENGTH: 6
<212> TYPE: PRT
<213> ORGANISM: Rattus norvegicus

<400> SEQUENCE: 16

His Cys Pro Gln Leu Glu
1 5

-continued

<210> SEQ ID NO 17
<211> LENGTH: 6
<212> TYPE: PRT
<213> ORGANISM: Rattus norvegicus

<400> SEQUENCE: 17

Gly Ser Val Thr His Tyr
1 5

<210> SEQ ID NO 18
<211> LENGTH: 6
<212> TYPE: PRT
<213> ORGANISM: Rattus norvegicus

<400> SEQUENCE: 18

Lys Leu Lys Leu Leu Glu
1 5

<210> SEQ ID NO 19
<211> LENGTH: 6
<212> TYPE: PRT
<213> ORGANISM: Rattus norvegicus

<400> SEQUENCE: 19

Ser Met Pro Ala Gly Ser
1 5

<210> SEQ ID NO 20
<211> LENGTH: 7
<212> TYPE: PRT
<213> ORGANISM: Homo sapiens

<400> SEQUENCE: 20

Met Leu Ile Leu Glu Cys Val
1 5

<210> SEQ ID NO 21
<211> LENGTH: 3144
<212> TYPE: PRT
<213> ORGANISM: Homo sapiens

<400> SEQUENCE: 21

Met Ala Thr Leu Glu Lys Leu Met Lys Ala Phe Glu Ser Leu Lys Ser
1 5 10 15

Phe Gln Gln Gln Gln Gln Gln Gln Gln Gln Gln Gln Gln Gln Gln Gln
20 25 30

Gln Gln Gln Gln Gln Gln Gln Gln Pro Pro Pro Pro Pro Pro Pro Pro
35 40 45

Pro Pro Pro Gln Leu Pro Gln Pro Pro Pro Gln Ala Gln Pro Leu Leu
50 55 60

Pro Gln Pro Gln Pro Pro Pro Pro Pro Pro Pro Pro Pro Pro Gly Pro
65 70 75 80

Ala Val Ala Glu Glu Pro Leu His Arg Pro Lys Lys Glu Leu Ser Ala
85 90 95

Thr Lys Lys Asp Arg Val Asn His Cys Leu Thr Ile Cys Glu Asn Ile
100 105 110

Val Ala Gln Ser Val Arg Asn Ser Pro Glu Phe Gln Lys Leu Leu Gly
115 120 125

Ile Ala Met Glu Leu Phe Leu Leu Cys Ser Asp Asp Ala Glu Ser Asp
130 135 140

-continued

```
Val Arg Met Val Ala Asp Glu Cys Leu Asn Lys Val Ile Lys Ala Leu
 145                 150                 155                 160

Met Asp Ser Asn Leu Pro Arg Leu Gln Leu Glu Leu Tyr Lys Glu Ile
                 165                 170                 175

Lys Lys Asn Gly Ala Pro Arg Ser Leu Arg Ala Ala Leu Trp Arg Phe
             180                 185                 190

Ala Glu Leu Ala His Leu Val Arg Pro Gln Lys Cys Arg Pro Tyr Leu
         195                 200                 205

Val Asn Leu Leu Pro Cys Leu Thr Arg Thr Ser Lys Arg Pro Glu Glu
     210                 215                 220

Ser Val Gln Glu Thr Leu Ala Ala Ala Val Pro Lys Ile Met Ala Ser
 225                 230                 235                 240

Phe Gly Asn Phe Ala Asn Asp Asn Glu Ile Lys Val Leu Leu Lys Ala
                 245                 250                 255

Phe Ile Ala Asn Leu Lys Ser Ser Ser Pro Thr Ile Arg Arg Thr Ala
             260                 265                 270

Ala Gly Ser Ala Val Ser Ile Cys Gln His Ser Arg Arg Thr Gln Tyr
         275                 280                 285

Phe Tyr Ser Trp Leu Leu Asn Val Leu Leu Gly Leu Leu Val Pro Val
     290                 295                 300

Glu Asp Glu His Ser Thr Leu Leu Ile Leu Gly Val Leu Leu Thr Leu
 305                 310                 315                 320

Arg Tyr Leu Val Pro Leu Leu Gln Gln Gln Val Lys Asp Thr Ser Leu
                 325                 330                 335

Lys Gly Ser Phe Gly Val Thr Arg Lys Glu Met Glu Val Ser Pro Ser
             340                 345                 350

Ala Glu Gln Leu Val Gln Val Tyr Glu Leu Thr Leu His His Thr Gln
         355                 360                 365

His Gln Asp His Asn Val Val Thr Gly Ala Leu Glu Leu Leu Gln Gln
     370                 375                 380

Leu Phe Arg Thr Pro Pro Pro Glu Leu Leu Gln Thr Leu Thr Ala Val
 385                 390                 395                 400

Gly Gly Ile Gly Gln Leu Thr Ala Ala Lys Glu Glu Ser Gly Gly Arg
                 405                 410                 415

Ser Arg Ser Gly Ser Ile Val Glu Leu Ile Ala Gly Gly Gly Ser Ser
             420                 425                 430

Cys Ser Pro Val Leu Ser Arg Lys Gln Lys Gly Lys Val Leu Leu Gly
         435                 440                 445

Glu Glu Glu Ala Leu Glu Asp Asp Ser Glu Ser Arg Ser Asp Val Ser
     450                 455                 460

Ser Ser Ala Leu Thr Ala Ser Val Lys Asp Glu Ile Ser Gly Glu Leu
 465                 470                 475                 480

Ala Ala Ser Ser Gly Val Ser Thr Pro Gly Ser Ala Gly His Asp Ile
                 485                 490                 495

Ile Thr Glu Gln Pro Arg Ser Gln His Thr Leu Gln Ala Asp Ser Val
             500                 505                 510

Asp Leu Ala Ser Cys Asp Leu Thr Ser Ser Ala Thr Asp Gly Asp Glu
         515                 520                 525

Glu Asp Ile Leu Ser His Ser Ser Ser Gln Val Ser Ala Val Pro Ser
     530                 535                 540

Asp Pro Ala Met Asp Leu Asn Asp Gly Thr Gln Ala Ser Ser Pro Ile
 545                 550                 555                 560

Ser Asp Ser Ser Gln Thr Thr Thr Glu Gly Pro Asp Ser Ala Val Thr
```

-continued

```
                565                 570                 575

Pro Ser Asp Ser Ser Glu Ile Val Leu Asp Gly Thr Asp Asn Gln Tyr
            580                 585                 590

Leu Gly Leu Gln Ile Gly Gln Pro Gln Asp Glu Asp Glu Glu Ala Thr
        595                 600                 605

Gly Ile Leu Pro Asp Glu Ala Ser Glu Ala Phe Arg Asn Ser Ser Met
    610                 615                 620

Ala Leu Gln Gln Ala His Leu Leu Lys Asn Met Ser His Cys Arg Gln
625                 630                 635                 640

Pro Ser Asp Ser Ser Val Asp Lys Phe Val Leu Arg Asp Glu Ala Thr
                645                 650                 655

Glu Pro Gly Asp Gln Glu Asn Lys Pro Cys Arg Ile Lys Gly Asp Ile
            660                 665                 670

Gly Gln Ser Thr Asp Asp Asp Ser Ala Pro Leu Val His Cys Val Arg
        675                 680                 685

Leu Leu Ser Ala Ser Phe Leu Leu Thr Gly Gly Lys Asn Val Leu Val
    690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
                725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly
        755                 760                 765

Ala Thr Ala Ile Leu Cys Gly Thr Leu Ile Cys Ser Ile Leu Ser Arg
    770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
                805                 810                 815

Leu Lys Asp Glu Ser Ser Val Thr Cys Lys Leu Ala Cys Thr Ala Val
            820                 825                 830

Arg Asn Cys Val Met Ser Leu Cys Ser Ser Ser Tyr Ser Glu Leu Gly
        835                 840                 845

Leu Gln Leu Ile Ile Asp Val Leu Thr Leu Arg Asn Ser Ser Tyr Trp
    850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
            900                 905                 910

Val Val Ile His Leu Leu Gly Asp Glu Asp Pro Arg Val Arg His Val
        915                 920                 925

Ala Ala Ala Ser Leu Ile Arg Leu Val Pro Lys Leu Phe Tyr Lys Cys
    930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
                965                 970                 975

Phe Ser Val Ser Thr Ile Thr Arg Ile Tyr Arg Gly Tyr Asn Leu Leu
            980                 985                 990
```

-continued

Pro Ser Ile Thr Asp Val Thr Met Glu Asn Asn Leu Ser Arg Val Ile
995 1000 1005

Ala Ala Val Ser His Glu Leu Ile Thr Ser Thr Thr Arg Ala Leu Thr
1010 1015 1020

Phe Gly Cys Cys Glu Ala Leu Cys Leu Leu Ser Thr Ala Phe Pro Val
1025 1030 1035 1040

Cys Ile Trp Ser Leu Gly Trp His Cys Gly Val Pro Pro Leu Ser Ala
1045 1050 1055

Ser Asp Glu Ser Arg Lys Ser Cys Thr Val Gly Met Ala Thr Met Ile
1060 1065 1070

Leu Thr Leu Leu Ser Ser Ala Trp Phe Pro Leu Asp Leu Ser Ala His
1075 1080 1085

Gln Asp Ala Leu Ile Leu Ala Gly Asn Leu Leu Ala Ala Ser Ala Pro
1090 1095 1100

Lys Ser Leu Arg Ser Ser Trp Ala Ser Glu Glu Glu Ala Asn Pro Ala
1105 1110 1115 1120

Ala Thr Lys Gln Glu Glu Val Trp Pro Ala Leu Gly Asp Arg Ala Leu
1125 1130 1135

Val Pro Met Val Glu Gln Leu Phe Ser His Leu Leu Lys Val Ile Asn
1140 1145 1150

Ile Cys Ala His Val Leu Asp Asp Val Ala Pro Gly Pro Ala Ile Lys
1155 1160 1165

Ala Ala Leu Pro Ser Leu Thr Asn Pro Pro Ser Leu Ser Pro Ile Arg
1170 1175 1180

Arg Lys Gly Lys Glu Lys Glu Pro Gly Glu Gln Ala Ser Val Pro Leu
1185 1190 1195 1200

Ser Pro Lys Lys Gly Ser Glu Ala Ser Ala Ala Ser Arg Gln Ser Asp
1205 1210 1215

Thr Ser Gly Pro Val Thr Thr Ser Lys Ser Ser Ser Leu Gly Ser Phe
1220 1225 1230

Tyr His Leu Pro Ser Tyr Leu Lys Leu His Asp Val Leu Lys Ala Thr
1235 1240 1245

His Ala Asn Tyr Lys Val Thr Leu Asp Leu Gln Asn Ser Thr Glu Lys
1250 1255 1260

Phe Gly Gly Phe Leu Arg Ser Ala Leu Asp Val Leu Ser Gln Ile Leu
1265 1270 1275 1280

Glu Leu Ala Thr Leu Gln Asp Ile Gly Lys Cys Val Glu Glu Ile Leu
1285 1290 1295

Gly Tyr Leu Lys Ser Cys Phe Ser Arg Glu Pro Met Met Ala Thr Val
1300 1305 1310

Cys Val Gln Gln Leu Leu Lys Thr Leu Phe Gly Thr Asn Leu Ala Ser
1315 1320 1325

Gln Phe Asp Gly Leu Ser Ser Asn Pro Ser Lys Ser Gln Gly Arg Ala
1330 1335 1340

Gln Arg Leu Gly Ser Ser Ser Val Arg Pro Gly Leu Tyr His Tyr Cys
1345 1350 1355 1360

Phe Met Ala Pro Tyr Thr His Phe Thr Gln Ala Leu Ala Asp Ala Ser
1365 1370 1375

Leu Arg Asn Met Val Gln Ala Glu Gln Glu Asn Asp Thr Ser Gly Trp
1380 1385 1390

Phe Asp Val Leu Gln Lys Val Ser Thr Gln Leu Lys Thr Asn Leu Thr
1395 1400 1405

-continued

Ser Val Thr Lys Asn Arg Ala Asp Lys Asn Ala Ile His Asn His Ile
1410 1415 1420

Arg Leu Phe Glu Pro Leu Val Ile Lys Ala Leu Lys Gln Tyr Thr Thr
1425 1430 1435 1440

Thr Thr Cys Val Gln Leu Gln Lys Gln Val Leu Asp Leu Leu Ala Gln
1445 1450 1455

Leu Val Gln Leu Arg Val Asn Tyr Cys Leu Leu Asp Ser Asp Gln Val
1460 1465 1470

Phe Ile Gly Phe Val Leu Lys Gln Phe Glu Tyr Ile Glu Val Gly Gln
1475 1480 1485

Phe Arg Glu Ser Glu Ala Ile Ile Pro Asn Ile Phe Phe Phe Leu Val
1490 1495 1500

Leu Leu Ser Tyr Glu Arg Tyr His Ser Lys Gln Ile Ile Gly Ile Pro
1505 1510 1515 1520

Lys Ile Ile Gln Leu Cys Asp Gly Ile Met Ala Ser Gly Arg Lys Ala
1525 1530 1535

Val Thr His Ala Ile Pro Ala Leu Gln Pro Ile Val His Asp Leu Phe
1540 1545 1550

Val Leu Arg Gly Thr Asn Lys Ala Asp Ala Gly Lys Glu Leu Glu Thr
1555 1560 1565

Gln Lys Glu Val Val Val Ser Met Leu Leu Arg Leu Ile Gln Tyr His
1570 1575 1580

Gln Val Leu Glu Met Phe Ile Leu Val Leu Gln Gln Cys His Lys Glu
1585 1590 1595 1600

Asn Glu Asp Lys Trp Lys Arg Leu Ser Arg Gln Ile Ala Asp Ile Ile
1605 1610 1615

Leu Pro Met Leu Ala Lys Gln Gln Met His Ile Asp Ser His Glu Ala
1620 1625 1630

Leu Gly Val Leu Asn Thr Leu Phe Glu Ile Leu Ala Pro Ser Ser Leu
1635 1640 1645

Arg Pro Val Asp Met Leu Leu Arg Ser Met Phe Val Thr Pro Asn Thr
1650 1655 1660

Met Ala Ser Val Ser Thr Val Gln Leu Trp Ile Ser Gly Ile Leu Ala
1665 1670 1675 1680

Ile Leu Arg Val Leu Ile Ser Gln Ser Thr Glu Asp Ile Val Leu Ser
1685 1690 1695

Arg Ile Gln Glu Leu Ser Phe Ser Pro Tyr Leu Ile Ser Cys Thr Val
1700 1705 1710

Ile Asn Arg Leu Arg Asp Gly Asp Ser Thr Ser Thr Leu Glu Glu His
1715 1720 1725

Ser Glu Gly Lys Gln Ile Lys Asn Leu Pro Glu Glu Thr Phe Ser Arg
1730 1735 1740

Phe Leu Leu Gln Leu Val Gly Ile Leu Leu Glu Asp Ile Val Thr Lys
1745 1750 1755 1760

Gln Leu Lys Val Glu Met Ser Glu Gln Gln His Thr Phe Tyr Cys Gln
1765 1770 1775

Glu Leu Gly Thr Leu Leu Met Cys Leu Ile His Ile Phe Lys Ser Gly
1780 1785 1790

Met Phe Arg Arg Ile Thr Ala Ala Ala Thr Arg Leu Phe Arg Ser Asp
1795 1800 1805

Gly Cys Gly Gly Ser Phe Tyr Thr Leu Asp Ser Leu Asn Leu Arg Ala
1810 1815 1820

Arg Ser Met Ile Thr Thr His Pro Ala Leu Val Leu Leu Trp Cys Gln

-continued

```
1825                1830                1835                1840

Ile Leu Leu Leu Val Asn His Thr Asp Tyr Arg Trp Trp Ala Glu Val
                1845                1850                1855

Gln Gln Thr Pro Lys Arg His Ser Leu Ser Ser Thr Lys Leu Leu Ser
            1860                1865                1870

Pro Gln Met Ser Gly Glu Glu Glu Asp Ser Asp Leu Ala Ala Lys Leu
        1875                1880                1885

Gly Met Cys Asn Arg Glu Ile Val Arg Arg Gly Ala Leu Ile Leu Phe
    1890                1895                1900

Cys Asp Tyr Val Cys Gln Asn Leu His Asp Ser Glu His Leu Thr Trp
1905                1910                1915                1920

Leu Ile Val Asn His Ile Gln Asp Leu Ile Ser Leu Ser His Glu Pro
                1925                1930                1935

Pro Val Gln Asp Phe Ile Ser Ala Val His Arg Asn Ser Ala Ala Ser
            1940                1945                1950

Gly Leu Phe Ile Gln Ala Ile Gln Ser Arg Cys Glu Asn Leu Ser Thr
        1955                1960                1965

Pro Thr Met Leu Lys Lys Thr Leu Gln Cys Leu Glu Gly Ile His Leu
    1970                1975                1980

Ser Gln Ser Gly Ala Val Leu Thr Leu Tyr Val Asp Arg Leu Leu Cys
1985                1990                1995                2000

Thr Pro Phe Arg Val Leu Ala Arg Met Val Asp Ile Leu Ala Cys Arg
                2005                2010                2015

Arg Val Glu Met Leu Leu Ala Ala Asn Leu Gln Ser Ser Met Ala Gln
            2020                2025                2030

Leu Pro Met Glu Glu Leu Asn Arg Ile Gln Glu Tyr Leu Gln Ser Ser
        2035                2040                2045

Gly Leu Ala Gln Arg His Gln Arg Leu Tyr Ser Leu Leu Asp Arg Phe
    2050                2055                2060

Arg Leu Ser Thr Met Gln Asp Ser Leu Ser Pro Ser Pro Pro Val Ser
2065                2070                2075                2080

Ser His Pro Leu Asp Gly Asp Gly His Val Ser Leu Glu Thr Val Ser
                2085                2090                2095

Pro Asp Lys Asp Trp Tyr Val His Leu Val Lys Ser Gln Cys Trp Thr
            2100                2105                2110

Arg Ser Asp Ser Ala Leu Leu Glu Gly Ala Glu Leu Val Asn Arg Ile
        2115                2120                2125

Pro Ala Glu Asp Met Asn Ala Phe Met Met Asn Ser Glu Phe Asn Leu
    2130                2135                2140

Ser Leu Leu Ala Pro Cys Leu Ser Leu Gly Met Ser Glu Ile Ser Gly
2145                2150                2155                2160

Gly Gln Lys Ser Ala Leu Phe Glu Ala Ala Arg Glu Val Thr Leu Ala
                2165                2170                2175

Arg Val Ser Gly Thr Val Gln Gln Leu Pro Ala Val His His Val Phe
            2180                2185                2190

Gln Pro Glu Leu Pro Ala Glu Pro Ala Ala Tyr Trp Ser Lys Leu Asn
        2195                2200                2205

Asp Leu Phe Gly Asp Ala Ala Leu Tyr Gln Ser Leu Pro Thr Leu Ala
    2210                2215                2220

Arg Ala Leu Ala Gln Tyr Leu Val Val Val Ser Lys Leu Pro Ser His
2225                2230                2235                2240

Leu His Leu Pro Pro Glu Lys Glu Lys Asp Ile Val Lys Phe Val Val
                2245                2250                2255
```

-continued

```
Ala Thr Leu Glu Ala Leu Ser Trp His Leu Ile His Glu Gln Ile Pro
            2260                2265                2270

Leu Ser Leu Asp Leu Gln Ala Gly Leu Asp Cys Cys Cys Leu Ala Leu
        2275                2280                2285

Gln Leu Pro Gly Leu Trp Ser Val Val Ser Ser Thr Glu Phe Val Thr
    2290                2295                2300

His Ala Cys Ser Leu Ile Tyr Cys Val His Phe Ile Leu Glu Ala Val
2305                2310                2315                2320

Ala Val Gln Pro Gly Glu Gln Leu Leu Ser Pro Glu Arg Arg Thr Asn
                2325                2330                2335

Thr Pro Lys Ala Ile Ser Glu Glu Glu Glu Glu Val Asp Pro Asn Thr
            2340                2345                2350

Gln Asn Pro Lys Tyr Ile Thr Ala Ala Cys Glu Met Val Ala Glu Met
        2355                2360                2365

Val Glu Ser Leu Gln Ser Val Leu Ala Leu Gly His Lys Arg Asn Ser
    2370                2375                2380

Gly Val Pro Ala Phe Leu Thr Pro Leu Leu Arg Asn Ile Ile Ile Ser
2385                2390                2395                2400

Leu Ala Arg Leu Pro Leu Val Asn Ser Tyr Thr Arg Val Pro Pro Leu
                2405                2410                2415

Val Trp Lys Leu Gly Trp Ser Pro Lys Pro Gly Gly Asp Phe Gly Thr
            2420                2425                2430

Ala Phe Pro Glu Ile Pro Val Glu Phe Leu Gln Glu Lys Glu Val Phe
        2435                2440                2445

Lys Glu Phe Ile Tyr Arg Ile Asn Thr Leu Gly Trp Thr Ser Arg Thr
    2450                2455                2460

Gln Phe Glu Glu Thr Trp Ala Thr Leu Leu Gly Val Leu Val Thr Gln
2465                2470                2475                2480

Pro Leu Val Met Glu Gln Glu Glu Ser Pro Pro Glu Glu Asp Thr Glu
                2485                2490                2495

Arg Thr Gln Ile Asn Val Leu Ala Val Gln Ala Ile Thr Ser Leu Val
            2500                2505                2510

Leu Ser Ala Met Thr Val Pro Val Ala Gly Asn Pro Ala Val Ser Cys
        2515                2520                2525

Leu Glu Gln Gln Pro Arg Asn Lys Pro Leu Lys Ala Leu Asp Thr Arg
    2530                2535                2540

Phe Gly Arg Lys Leu Ser Ile Ile Arg Gly Ile Val Glu Gln Glu Ile
2545                2550                2555                2560

Gln Ala Met Val Ser Lys Arg Glu Asn Ile Ala Thr His His Leu Tyr
                2565                2570                2575

Gln Ala Trp Asp Pro Val Pro Ser Leu Ser Pro Ala Thr Thr Gly Ala
            2580                2585                2590

Leu Ile Ser His Glu Lys Leu Leu Leu Gln Ile Asn Pro Glu Arg Glu
        2595                2600                2605

Leu Gly Ser Met Ser Tyr Lys Leu Gly Gln Val Ser Ile His Ser Val
    2610                2615                2620

Trp Leu Gly Asn Ser Ile Thr Pro Leu Arg Glu Glu Glu Trp Asp Glu
2625                2630                2635                2640

Glu Glu Glu Glu Glu Ala Asp Ala Pro Ala Pro Ser Ser Pro Pro Thr
                2645                2650                2655

Ser Pro Val Asn Ser Arg Lys His Arg Ala Gly Val Asp Ile His Ser
            2660                2665                2670
```

-continued

```
Cys Ser Gln Phe Leu Leu Glu Leu Tyr Ser Arg Trp Ile Leu Pro Ser
        2675                2680                2685

Ser Ser Ala Arg Arg Thr Pro Ala Ile Leu Ile Ser Glu Val Val Arg
    2690                2695                2700

Ser Leu Leu Val Val Ser Asp Leu Phe Thr Glu Arg Asn Gln Phe Glu
2705                2710                2715                2720

Leu Met Tyr Val Thr Leu Thr Glu Leu Arg Arg Val His Pro Ser Glu
                2725                2730                2735

Asp Glu Ile Leu Ala Gln Tyr Leu Val Pro Ala Thr Cys Lys Ala Ala
            2740                2745                2750

Ala Val Leu Gly Met Asp Lys Ala Val Ala Glu Pro Val Ser Arg Leu
        2755                2760                2765

Leu Glu Ser Thr Leu Arg Ser Ser His Leu Pro Ser Arg Val Gly Ala
    2770                2775                2780

Leu His Gly Val Leu Tyr Val Leu Glu Cys Asp Leu Leu Asp Asp Thr
2785                2790                2795                2800

Ala Lys Gln Leu Ile Pro Val Ile Ser Asp Tyr Leu Leu Ser Asn Leu
                2805                2810                2815

Lys Gly Ile Ala His Cys Val Asn Ile His Ser Gln Gln His Val Leu
            2820                2825                2830

Val Met Cys Ala Thr Ala Phe Tyr Leu Ile Glu Asn Tyr Pro Leu Asp
        2835                2840                2845

Val Gly Pro Glu Phe Ser Ala Ser Ile Ile Gln Met Cys Gly Val Met
    2850                2855                2860

Leu Ser Gly Ser Glu Glu Ser Thr Pro Ser Ile Ile Tyr His Cys Ala
2865                2870                2875                2880

Leu Arg Gly Leu Glu Arg Leu Leu Leu Ser Glu Gln Leu Ser Arg Leu
                2885                2890                2895

Asp Ala Glu Ser Leu Val Lys Leu Ser Val Asp Arg Val Asn Val His
            2900                2905                2910

Ser Pro His Arg Ala Met Ala Ala Leu Gly Leu Met Leu Thr Cys Met
        2915                2920                2925

Tyr Thr Gly Lys Glu Lys Val Ser Pro Gly Arg Thr Ser Asp Pro Asn
    2930                2935                2940

Pro Ala Ala Pro Asp Ser Glu Ser Val Ile Val Ala Met Glu Arg Val
2945                2950                2955                2960

Ser Val Leu Phe Asp Arg Ile Arg Lys Gly Phe Pro Cys Glu Ala Arg
                2965                2970                2975

Val Val Ala Arg Ile Leu Pro Gln Phe Leu Asp Asp Phe Phe Pro Pro
            2980                2985                2990

Gln Asp Ile Met Asn Lys Val Ile Gly Glu Phe Leu Ser Asn Gln Gln
        2995                3000                3005

Pro Tyr Pro Gln Phe Met Ala Thr Val Val Tyr Lys Val Phe Gln Thr
    3010                3015                3020

Leu His Ser Thr Gly Gln Ser Ser Met Val Arg Asp Trp Val Met Leu
3025                3030                3035                3040

Ser Leu Ser Asn Phe Thr Gln Arg Ala Pro Val Ala Met Ala Thr Trp
                3045                3050                3055

Ser Leu Ser Cys Phe Phe Val Ser Ala Ser Thr Ser Pro Trp Val Ala
            3060                3065                3070

Ala Ile Leu Pro His Val Ile Ser Arg Met Gly Lys Leu Glu Gln Val
        3075                3080                3085

Asp Val Asn Leu Phe Cys Leu Val Ala Thr Asp Phe Tyr Arg His Gln
```

-continued

```
     3090                3095                3100

Ile Glu Glu Glu Leu Asp Arg Arg Ala Phe Gln Ser Val Leu Glu Val
 3105                3110                3115                3120

Val Ala Ala Pro Gly Ser Pro Tyr His Arg Leu Leu Thr Cys Leu Arg
                 3125                3130                3135

Asn Val His Lys Val Thr Thr Cys
             3140


<210> SEQ ID NO 22
<211> LENGTH: 599
<212> TYPE: PRT
<213> ORGANISM: Rattus norvegicus

<400> SEQUENCE: 22

Met Arg Pro Lys Asp Gln Val Gln Ser Ser Ala Gly Asp Gly Thr Gly
  1               5                  10                  15

Ser Gly Asp Pro Ala Thr Gly Thr Pro Thr Thr Gln Pro Ala Ala Asp
             20                  25                  30

Pro Ala Pro Glu Pro Ser Ala Glu Pro Lys Pro Ala Pro Ala Gln Gly
         35                  40                  45

Thr Gly Ser Gly Gln Lys Ser Gly Ser Arg Thr Lys Thr Gly Gly Ser
     50                  55                  60

Phe Cys Arg Ser Arg Ile Arg Gly Asp Ser Asp Ala Pro Trp Thr Arg
 65                  70                  75                  80

Tyr Ile Phe Gln Gly Pro Tyr Gly Pro Arg Ala Thr Gly Leu Gly Thr
                 85                  90                  95

Gly Arg Ala Glu Gly Ile Trp Lys Thr Pro Ala Ala Tyr Ile Gly Arg
            100                 105                 110

Arg Pro Gly Val Ser Gly Pro Glu Arg Ala Ala Phe Ile Arg Glu Leu
        115                 120                 125

Gln Glu Ala Leu Cys Pro Asn Pro Leu Pro Arg Lys Lys Ile Thr Glu
    130                 135                 140

Asp Asp Ile Lys Val Met Leu Tyr Leu Leu Glu Glu Lys Glu Arg Asp
145                 150                 155                 160

Leu Asn Thr Ala Ala Arg Ile Gly Gln Ser Leu Val Lys Gln Asn Ser
                165                 170                 175

Val Leu Met Glu Glu Asn Asn Lys Leu Glu Thr Met Leu Gly Ser Ala
            180                 185                 190

Arg Glu Glu Ile Leu His Leu Arg Lys Gln Val Asn Leu Arg Asp Asp
        195                 200                 205

Leu Leu Gln Leu Tyr Ser Asp Ser Asp Asp Asp Glu Glu Asp Glu Glu
    210                 215                 220

Asp Glu Glu Glu Glu Glu Gly Glu Glu Glu Glu Arg Glu Gly Gln Arg
225                 230                 235                 240

Asp Gln Asp Gln Gln His Asp His Pro Tyr Gly Ala Pro Lys Pro Pro
                245                 250                 255

Pro Lys Ala Glu Thr Leu His His Cys Pro Gln Leu Glu Ala Leu Lys
            260                 265                 270

Gln Lys Leu Lys Leu Leu Glu Glu Glu Asn Asp His Leu Arg Glu Glu
        275                 280                 285

Ala Ser His Leu Asp Asn Leu Glu Asp Lys Glu Gln Met Leu Ile Leu
    290                 295                 300

Glu Cys Val Glu Gln Phe Ser Glu Ala Ser Gln Gln Met Ala Glu Leu
305                 310                 315                 320
```

-continued

```
Ser Glu Val Leu Val Leu Arg Leu Glu Gly Tyr Glu Arg Gln Gln Lys
                325                 330                 335

Glu Ile Thr Gln Leu Gln Ala Glu Ile Thr Lys Leu Gln Gln Arg Cys
            340                 345                 350

Gln Ser Tyr Gly Ala Gln Thr Glu Lys Leu Gln Gln Gln Leu Ala Ser
        355                 360                 365

Glu Lys Gly Val His Pro Glu Ser Leu Arg Ala Gly Ser His Met Gln
    370                 375                 380

Asp Tyr Gly Ser Arg Pro Arg Glu Arg Gln Glu Asp Gly Lys Ser His
385                 390                 395                 400

Arg Gln Arg Ser Ser Met Pro Ala Gly Ser Val Thr His Tyr Gly Tyr
                405                 410                 415

Ser Val Pro Leu Asp Ala Leu Pro Ser Phe Pro Glu Thr Leu Ala Glu
            420                 425                 430

Glu Leu Arg Thr Ser Leu Arg Lys Phe Ile Thr Asp Pro Ala Tyr Phe
        435                 440                 445

Met Glu Arg Cys Asp Thr Arg Cys Arg Glu Glu Arg Lys Lys Glu Gln
    450                 455                 460

Gly Thr Met Pro Pro Pro Pro Val Gln Asp Leu Lys Pro Pro Glu Asp
465                 470                 475                 480

Phe Glu Ala Pro Glu Glu Leu Val Pro Glu Glu Glu Leu Gly Ala Ile
                485                 490                 495

Glu Glu Val Gly Thr Ala Glu Asp Gly Pro Ala Glu Glu Thr Glu Gln
            500                 505                 510

Ala Ser Glu Glu Thr Glu Ala Trp Glu Glu Val Glu Pro Glu Val Asp
        515                 520                 525

Glu Ala Thr Arg Met Asn Val Val Val Ser Ala Leu Glu Ala Ser Gly
    530                 535                 540

Leu Gly Pro Ser His Leu Asp Met Lys Tyr Val Leu Gln Gln Leu Ser
545                 550                 555                 560

Asn Trp Gln Asp Ala His Ser Lys Arg Gln Gln Lys Gln Lys Val Val
                565                 570                 575

Pro Lys Gly Glu Cys Ser Arg Arg Gly His Pro Pro Ala Ser Gly Thr
            580                 585                 590

Ser Tyr Arg Ser Ser Thr Leu
        595


<210> SEQ ID NO 23
<211> LENGTH: 629
<212> TYPE: PRT
<213> ORGANISM: Rattus norvegicus

<400> SEQUENCE: 23

Met Arg Pro Lys Asp Gln Val Gln Ser Ser Ala Gly Asp Gly Thr Gly
 1               5                  10                  15

Ser Gly Asp Pro Ala Thr Gly Thr Pro Thr Thr Gln Pro Ala Ala Asp
            20                  25                  30

Pro Ala Pro Glu Pro Ser Ala Glu Pro Lys Pro Ala Pro Ala Gln Gly
        35                  40                  45

Thr Gly Ser Gly Gln Lys Ser Gly Ser Arg Thr Lys Thr Gly Gly Ser
    50                  55                  60

Phe Cys Arg Ser Arg Ile Arg Gly Asp Ser Asp Ala Pro Trp Thr Arg
65                  70                  75                  80

Tyr Ile Phe Gln Gly Pro Tyr Gly Pro Arg Ala Thr Gly Leu Gly Thr
                85                  90                  95
```

-continued

```
Gly Arg Ala Glu Gly Ile Trp Lys Thr Pro Ala Ala Tyr Ile Gly Arg
            100                 105                 110

Arg Pro Gly Val Ser Gly Pro Glu Arg Ala Ala Phe Ile Arg Glu Leu
        115                 120                 125

Gln Glu Ala Leu Cys Pro Asn Pro Leu Pro Arg Lys Lys Ile Thr Glu
    130                 135                 140

Asp Asp Ile Lys Val Met Leu Tyr Leu Leu Glu Glu Lys Glu Arg Asp
145                 150                 155                 160

Leu Asn Thr Ala Ala Arg Ile Gly Gln Ser Leu Val Lys Gln Asn Ser
                165                 170                 175

Val Leu Met Glu Glu Asn Asn Lys Leu Glu Thr Met Leu Gly Ser Ala
            180                 185                 190

Arg Glu Glu Ile Leu His Leu Arg Lys Gln Val Asn Leu Arg Asp Asp
        195                 200                 205

Leu Leu Gln Leu Tyr Ser Asp Ser Asp Asp Asp Glu Glu Asp Glu Glu
    210                 215                 220

Asp Glu Glu Glu Glu Glu Gly Glu Glu Glu Glu Arg Glu Gly Gln Arg
225                 230                 235                 240

Asp Gln Asp Gln Gln His Asp His Pro Tyr Gly Ala Pro Lys Pro Pro
                245                 250                 255

Pro Lys Ala Glu Thr Leu His His Cys Pro Gln Leu Glu Ala Leu Lys
            260                 265                 270

Gln Lys Leu Lys Leu Leu Glu Glu Glu Asn Asp His Leu Arg Glu Glu
        275                 280                 285

Ala Ser His Leu Asp Asn Leu Glu Asp Lys Glu Gln Met Leu Ile Leu
    290                 295                 300

Glu Cys Val Glu Gln Phe Ser Glu Ala Ser Gln Gln Met Ala Glu Leu
305                 310                 315                 320

Ser Glu Val Leu Val Leu Arg Leu Glu Gly Tyr Glu Arg Gln Gln Lys
                325                 330                 335

Glu Ile Thr Gln Leu Gln Ala Glu Ile Thr Lys Leu Gln Gln Arg Cys
            340                 345                 350

Gln Ser Tyr Gly Ala Gln Thr Glu Lys Leu Gln Gln Gln Leu Ala Ser
        355                 360                 365

Glu Lys Gly Val His Pro Glu Ser Leu Arg Ala Gly Ser His Met Gln
    370                 375                 380

Asp Tyr Gly Ser Arg Pro Arg Glu Arg Gln Glu Asp Gly Lys Ser His
385                 390                 395                 400

Arg Gln Arg Ser Ser Met Pro Ala Gly Ser Val Thr His Tyr Gly Tyr
                405                 410                 415

Ser Val Pro Leu Asp Ala Leu Pro Ser Phe Pro Glu Thr Leu Ala Glu
            420                 425                 430

Glu Leu Arg Thr Ser Leu Arg Lys Phe Ile Thr Asp Pro Ala Tyr Phe
        435                 440                 445

Met Glu Arg Cys Asp Thr Arg Cys Arg Glu Glu Arg Lys Lys Glu Gln
    450                 455                 460

Gly Thr Met Pro Pro Pro Pro Val Gln Asp Leu Lys Pro Pro Glu Asp
465                 470                 475                 480

Phe Glu Ala Pro Glu Glu Leu Val Pro Glu Glu Glu Leu Gly Ala Ile
                485                 490                 495

Glu Glu Val Gly Thr Ala Glu Asp Gly Pro Ala Glu Glu Thr Glu Gln
            500                 505                 510
```

-continued

Ala Ser Glu Glu Thr Glu Ala Trp Glu Glu Val Glu Pro Glu Val Asp
        515                 520                 525

Glu Ala Thr Arg Met Asn Val Val Val Ser Ala Leu Glu Ala Ser Gly
    530                 535                 540

Leu Gly Pro Ser His Leu Asp Met Lys Tyr Val Leu Gln Gln Leu Ser
545                 550                 555                 560

Asn Trp Gln Asp Ala His Ser Lys Arg Gln Gln Lys Gln Lys Val Val
                565                 570                 575

Pro Lys Asp Ser Pro Ala Pro Gln Gln Gln Thr Asn Met Gly Gly Gly
            580                 585                 590

Ile Val Glu Gln Gln Pro Ile Val Pro Thr Gln Asp Ser Gln Arg Leu
        595                 600                 605

Glu Glu Asp Arg Ala Thr His Ser Pro Ser Ala Arg Glu Glu Glu Gly
    610                 615                 620

Pro Ser Gly Ala Thr
625

<210> SEQ ID NO 24
<211> LENGTH: 126
<212> TYPE: PRT
<213> ORGANISM: Homo sapiens

<400> SEQUENCE: 24

Glu Glu Glu Asn His Gln Leu Arg Glu Glu Ala Ser Gln Leu Asp Thr
 1               5                  10                  15

Leu Glu Asp Glu Glu Gln Met Leu Ile Leu Glu Cys Val Glu Gln Phe
            20                  25                  30

Ser Glu Ala Ser Gln Gln Met Ala Glu Leu Ser Glu Val Leu Val Leu
        35                  40                  45

Arg Leu Glu Gly Tyr Glu Arg Gln Gln Lys Glu Ile Thr Gln Leu Gln
    50                  55                  60

Ala Glu Ile Thr Lys Leu Gln Gln Arg Cys Gln Ser Tyr Gly Ala Gln
65                  70                  75                  80

Thr Glu Lys Leu Gln Gln Gln Leu Ala Ser Glu Lys Gly Val His Pro
                85                  90                  95

Glu Ser Leu Arg Ala Gly Ser His Met Gln Asp Tyr Gly Ser Arg Pro
            100                 105                 110

Arg Glu Arg Gln Glu Asp Gly Lys Ser His Arg Gln Arg Ser
        115                 120                 125

<210> SEQ ID NO 25
<211> LENGTH: 331
<212> TYPE: PRT
<213> ORGANISM: Homo sapiens

<400> SEQUENCE: 25

Asp Asp Leu Leu Gln Leu Tyr Ser Asp Ser Asp Glu Glu Asp Glu Asp
 1               5                  10                  15

Glu Glu Glu Glu Glu Glu Glu Lys Glu Ala Glu Glu Glu Gln Glu Glu
            20                  25                  30

Glu Glu Ala Glu Glu Asp Leu Gln Cys Ala His Pro Cys Asp Ala Pro
        35                  40                  45

Lys Leu Ile Ser Gln Glu Ala Leu Leu His Gln His His Cys Pro Gln
    50                  55                  60

Leu Glu Ala Leu Gln Glu Lys Leu Arg Leu Leu Glu Glu Glu Asn His
65                  70                  75                  80

-continued

```
Gln Leu Arg Glu Glu Ala Ser Gln Leu Asp Thr Leu Glu Asp Glu Glu
                85                  90                  95

Gln Met Leu Ile Leu Glu Cys Val Glu Gln Phe Ser Glu Ala Ser Gln
            100                 105                 110

Gln Met Ala Glu Leu Ser Glu Val Leu Val Leu Arg Leu Glu Asn Tyr
        115                 120                 125

Glu Arg Gln Gln Gln Glu Val Ala Arg Leu Gln Ala Gln Val Leu Lys
    130                 135                 140

Leu Gln Gln Arg Cys Arg Met Tyr Gly Ala Glu Thr Glu Lys Leu Gln
145                 150                 155                 160

Lys Gln Leu Ala Ser Glu Lys Glu Ile Gln Met Gln Leu Gln Glu Glu
                165                 170                 175

Glu Thr Leu Pro Gly Phe Gln Glu Thr Leu Ala Glu Glu Leu Arg Thr
            180                 185                 190

Ser Leu Arg Arg Met Ile Ser Asp Pro Val Tyr Phe Met Glu Arg Asn
        195                 200                 205

Tyr Glu Met Pro Arg Gly Asp Thr Ser Ser Leu Arg Tyr Asp Phe Arg
    210                 215                 220

Tyr Ser Glu Asp Arg Glu Gln Val Arg Gly Phe Glu Ala Glu Glu Gly
225                 230                 235                 240

Leu Met Leu Ala Ala Asp Ile Met Arg Gly Glu Asp Phe Thr Pro Ala
                245                 250                 255

Glu Glu Leu Val Pro Gln Glu Glu Leu Gly Ala Ala Lys Lys Val Pro
            260                 265                 270

Ala Glu Glu Gly Val Met Glu Glu Ala Glu Leu Val Ser Glu Glu Thr
        275                 280                 285

Glu Gly Trp Glu Glu Val Glu Leu Glu Leu Asp Glu Ala Thr Arg Met
    290                 295                 300

Asn Val Val Thr Ser Thr Leu Glu Ala Ser Gly Leu Gly Pro Ser His
305                 310                 315                 320

Leu Asp Met Asn Tyr Val Leu Gln Gln Leu Ser
                325                 330
```